United States Patent [19]
Barker et al.

[11] Patent Number: 5,876,116
[45] Date of Patent: Mar. 2, 1999

[54] INTEGRATED BONE CEMENT MIXING AND DISPENSING SYSTEM

[76] Inventors: Donald Barker, 8 Mountain Laurel La., Sandy Hook, Conn. 06482; James P. Seaton, 116 Fairmont Ave., Chatham, N.J. 07929

[21] Appl. No.: 752,003

[22] Filed: Nov. 15, 1996

[51] Int. Cl.⁶ .............................. B01F 7/16; B01F 15/02; G01F 11/42
[52] U.S. Cl. ...................... 366/182.3; 366/139; 366/189; 366/195; 222/241; 604/93
[58] Field of Search .................. 366/139, 154.1, 366/155.1, 182.1, 182.3, 182.4, 189, 192, 194, 242, 244, 245, 195; 222/236, 239, 241; 604/93, 131

[56] References Cited

U.S. PATENT DOCUMENTS

| | | | |
|---|---|---|---|
| 346,265 | 7/1886 | Charlton et al. | 222/241 |
| 1,204,111 | 11/1916 | Anderson | 222/239 |
| 1,898,851 | 2/1933 | Pieretti | 222/239 |
| 4,146,334 | 3/1979 | Farrell | 366/192 |
| 4,277,184 | 7/1981 | Solomon | 366/139 |
| 4,671,263 | 6/1987 | Draenert . | |
| 5,071,040 | 12/1991 | Laptewicz, Jr. . | |
| 5,193,907 | 3/1993 | Faccioli et al. . | |
| 5,344,232 | 9/1994 | Nelson et al. | 366/139 |
| 5,435,645 | 7/1995 | Faccioli et al. . | |
| 5,494,349 | 2/1996 | Seddon . | |

*Primary Examiner*—Tony G. Soohoo
*Attorney, Agent, or Firm*—Melvin I. Stoltz

[57] ABSTRACT

By providing a single housing comprising a mixing chamber integrally combined with a delivery chamber or tube, a unitary, fully integrated, bone cement mixing and dispensing system is attained which eliminates user exposure or handling of the mixed bone cement. In the present invention, the two chambers of the integrated system of the present invention are movable between two alternate positions, a first position wherein each chamber is sealed from the other, and a second position wherein the two chambers are in direct communication with each other. In this way, the mixing chamber is operated independently of the delivery chamber for preparing the bone cement and, once prepared, easily transferred from the mixing chamber through the delivery chamber for immediate use.

34 Claims, 11 Drawing Sheets

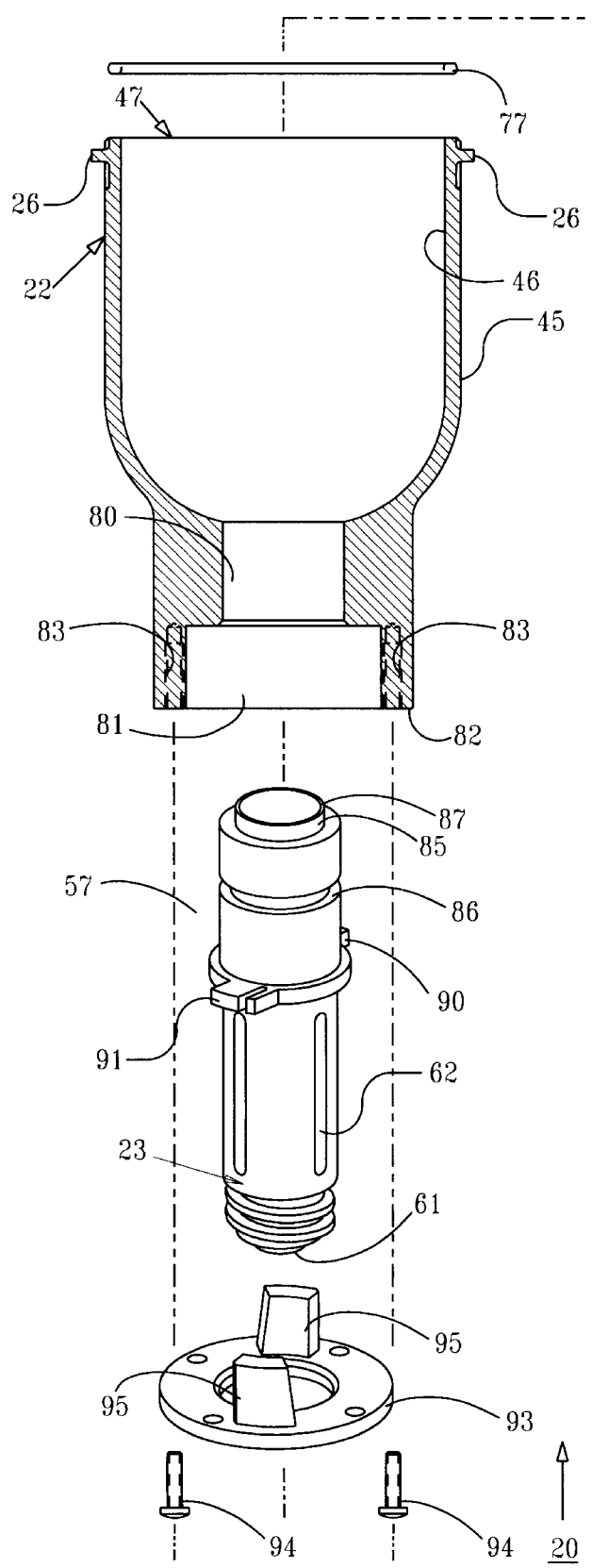
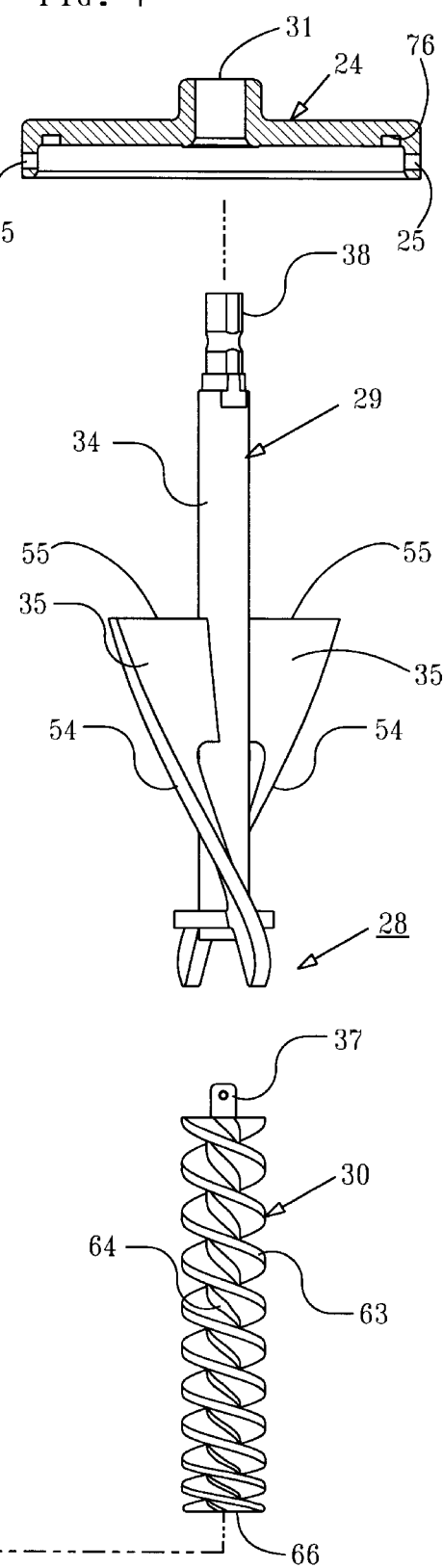
FIG. 7

FIG. 12
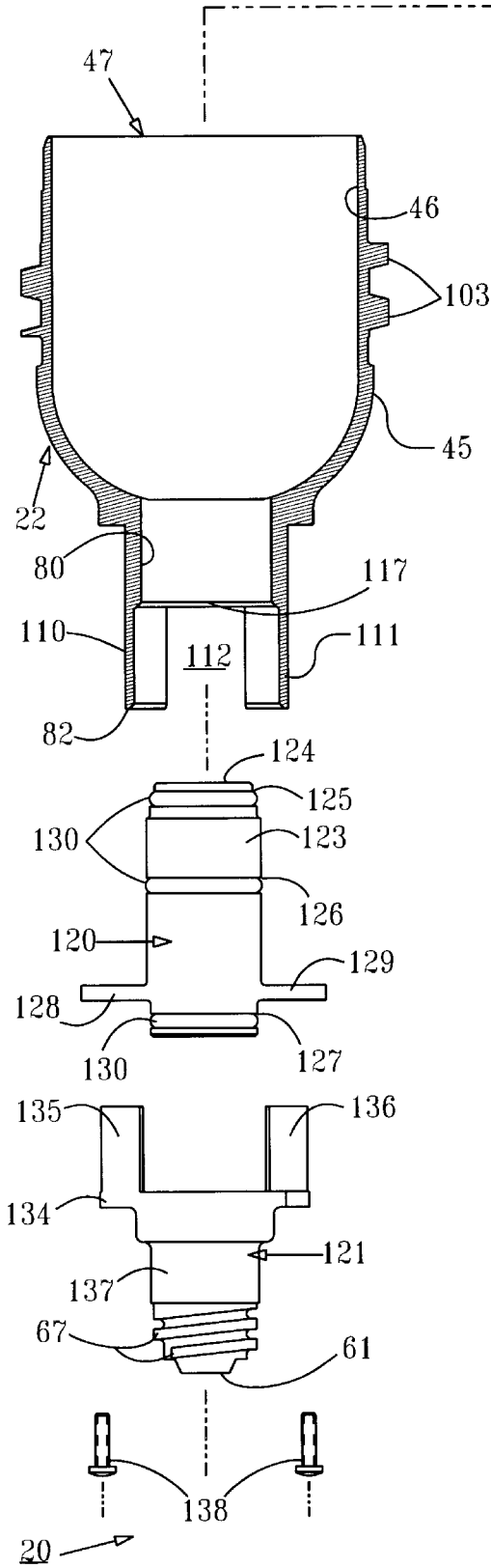
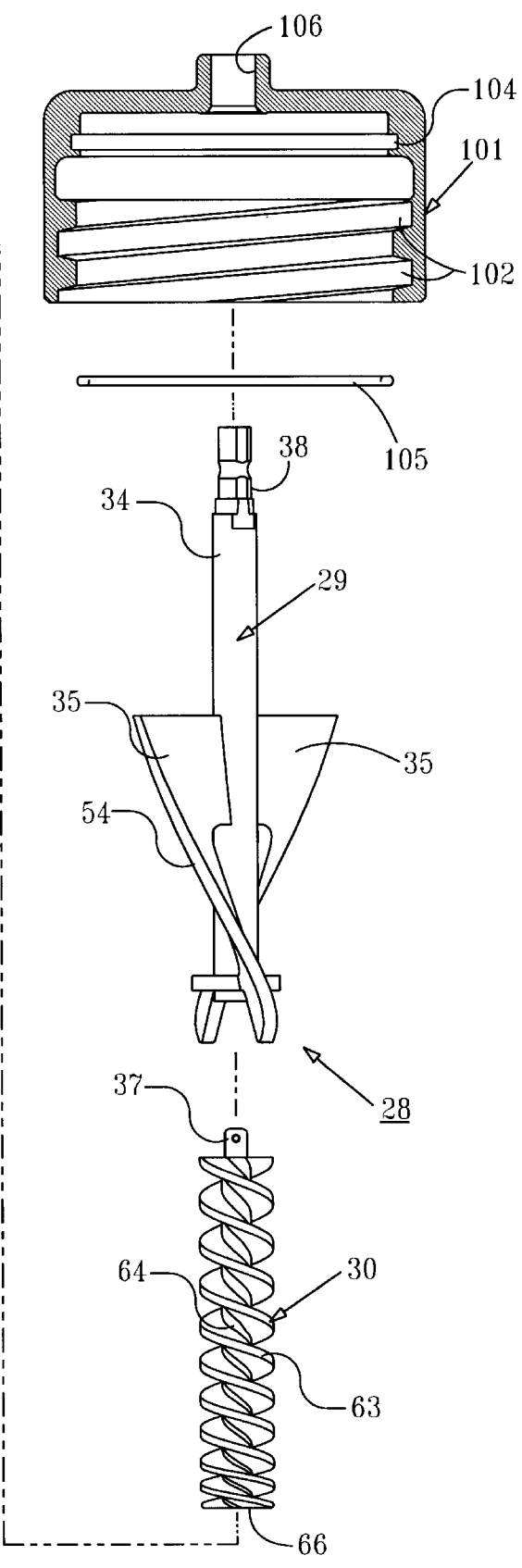

FIG. 13
FIG. 14
FIG. 15
FIG. 16
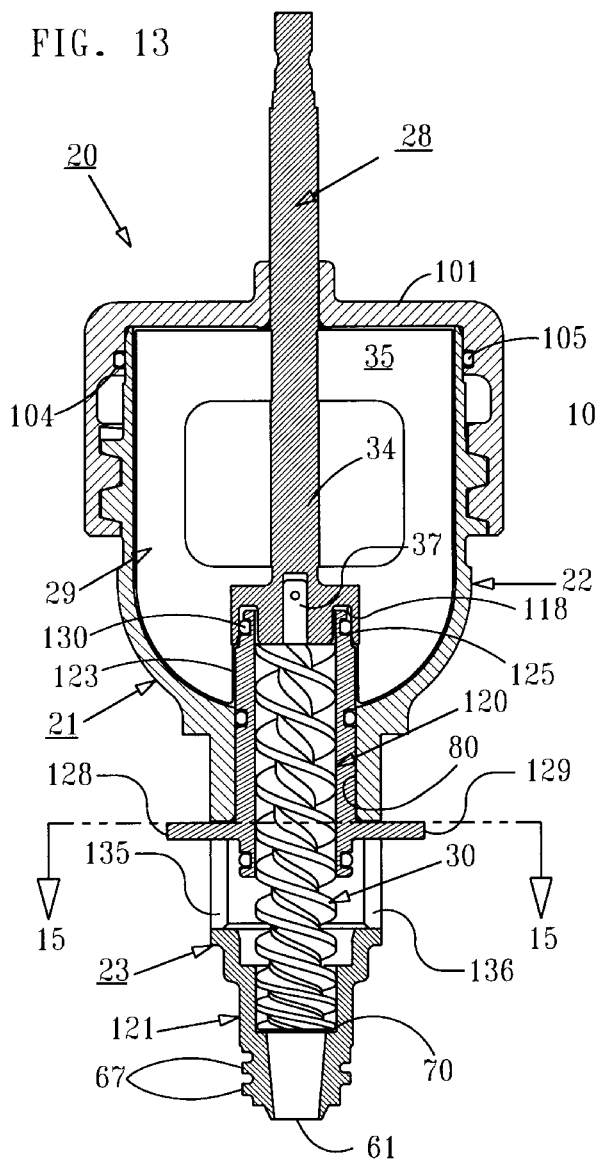
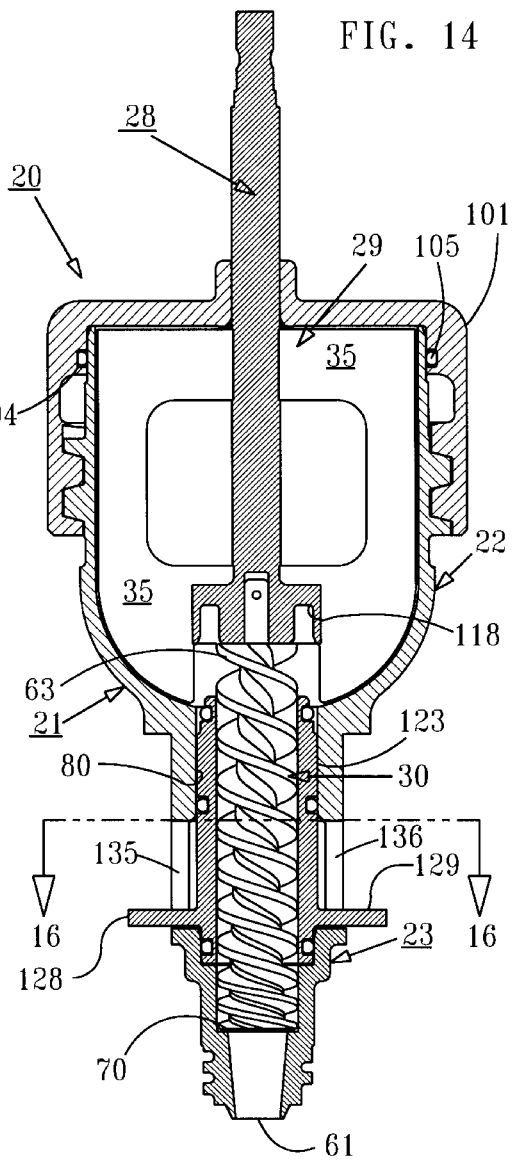
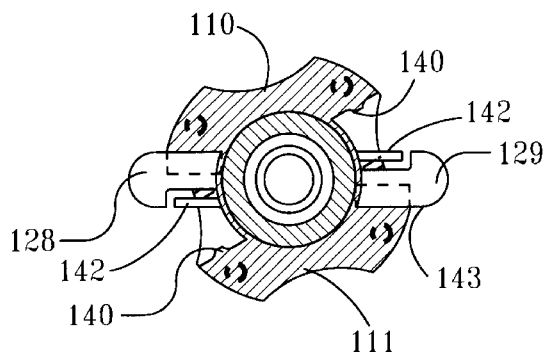
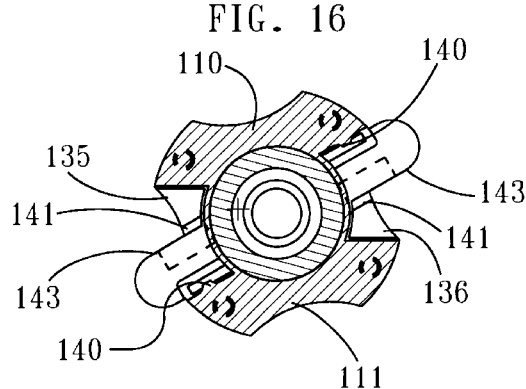

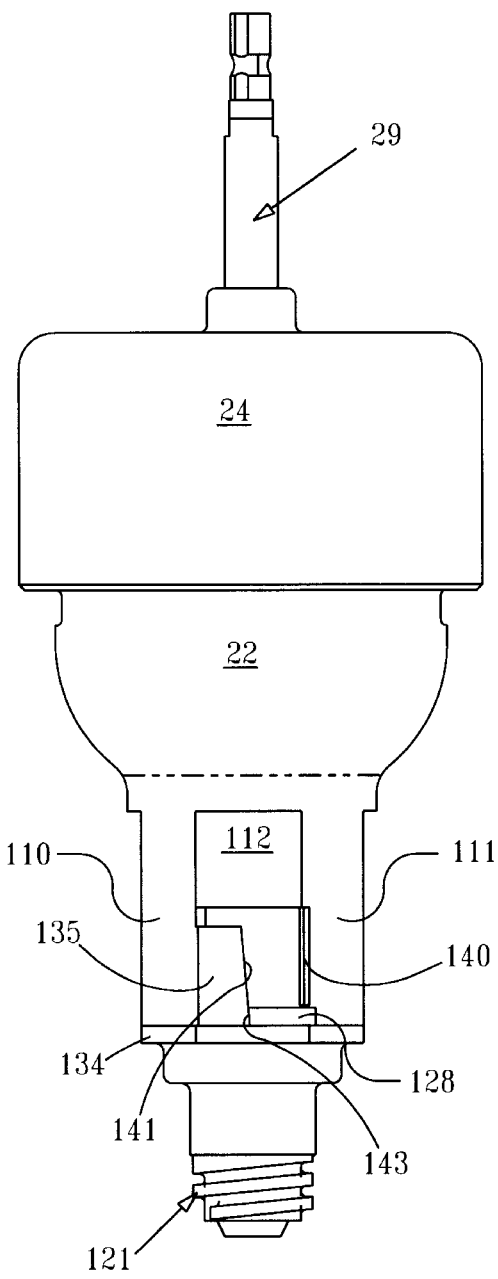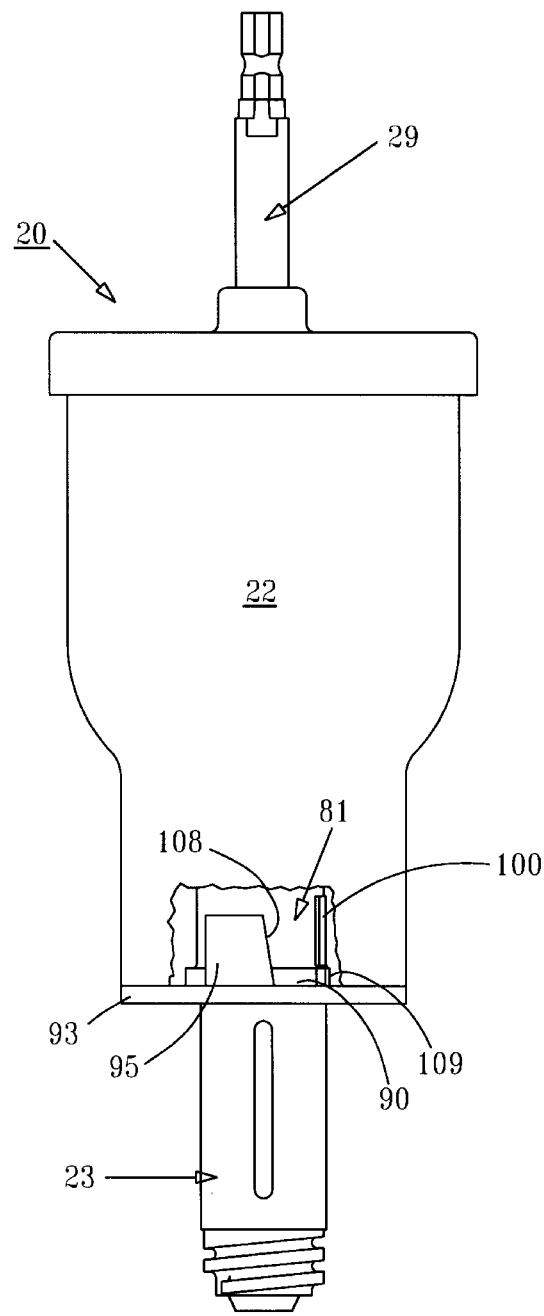

INTEGRATED BONE CEMENT MIXING AND DISPENSING SYSTEM

TECHNICAL FIELD

This invention relates to a system or apparatus for mixing a two-part bone cement, formulated for surgical applications in securing prosthetic devices to bones and joints, and more particularly, to a fully integrated, unitary system capable of providing mixing of the two-part bone cement, automatic transfer of the mixed cement to a dispensing zone, and dispensing of the cement directly to the desired site under pressure. In addition, this invention relates to a system or apparatus for dispensing a premixed bone cement, with the system providing for the removal of air in the mix and dispense the material into the dispensing zone with adequate pressure to asure a good interlock of the material to the bone and prothesis.

BACKGROUND ART

In many surgical procedures, particularly orthopedic procedures, it has now become common to affix a prosthesis to a bone or joint structure for improving the strength, rigidity, and movement of the bone/joint structure. Although such prosthetic devices have been widely used, hip joints and knee joints are the most common examples of areas where prosthetic devices are used to reduce or eliminate pain and suffering that exists from typical leg movements.

As part of these operations, it has become common practice to secure the prosthesis to the bone or joint using a cement, formed by intermixing a powder and a liquid. Once intermixed, the two components must be thoroughly blended together to achieve the required consistency for the fully mixed cement, with the fully mixed cement then being loaded into a dispensing apparatus for placement in the desired area for affixing the prosthesis to the desired site.

In most applications, the two components forming the cement are mixed in a mixing vessel and, once fully mixed, are manually transferred from the mixing vessel to a dispensing member. Typically, devices such as caulking guns are employed, for dispensing the fully mixed cement to the precisely desired location of the patient. This process is extremely unpleasant for individuals mixing the cement, since the mixed cement contains an offensive, noxious odor. Furthermore, removal of the mixed cement from the mixing vessel into the caulking gun is cumbersome, time consuming, and has the potential for being mishandled and/or dropped.

Another problem typically encountered with prior art systems is the difficulty encountered with air being entrapped in the mixed cement. The presence of air pockets or air bubbles in the mixed cement is undesirable. Since it is important that the cement added to the bone area for affixing the prosthetic be virtually free of any entrapped air bubbles or air pockets, most prior art systems demand mixing of the powder and liquid under vacuum conditions. As a result, added limitations are incurred on the flexibility of the mixing vessel and the ability to mix the two-part cement mixture in any desired location.

Although attempts have been made to reduce or eliminate some of these prior art problems, no prior art systems has been developed which completely eliminates the requirement for vacuum or the requirement for two separate components for mixing and dispensing. At best, some prior art systems have enabled the mixing to be performed in one vessel which then is directly connected to a feeding system for enabling the mixed cement to be added to a holding tube for use with the dispensing caulking gun. However, a separate dispensing system is required and extra handling and exposure of the mixed cement to the surrounding personnel is required. Furthermore, care must be exercised during the transfer of the mixed cement to the dispenser, since air is frequently introduced into the cement during this transfer operation as well as the risk of dropping or spilling the material.

Therefore, it is a principal object of the present invention to provide a bone cement mixing and dispensing system which comprises a fully integrated, unitary structure which eliminates the requirement for independent transfer of the mixed cement to a dispensing member.

Another object of the present invention is to provide a unitary, integrated, mixing and dispensing system for bone cement having the characteristic features described above which is easy to use and is virtually fool-proof in its operation.

Another object of the present invention is to provide a unitary, integrated, mixing and dispensing system for bone cement having the characteristic features described above which provides intermixed bone cement virtually devoid of entrapped air pockets or air bubbles while eliminating the need for mixing under vacuum but enabling vacuum to be used, if desired.

Another object of the present invention is to provide a unitary, integrated, mixing and dispensing system for bone cement having the characteristic features described above which is easily employed by any individual, free from unwanted odors and product handling difficulties.

Other and more specific objects will in part be obvious and will in part appear hereinafter.

SUMMARY OF THE INVENTION

By employing the present invention, all of the drawbacks and difficulties encountered with prior art systems are eliminated and a unitary, fully integrated, bone cement mixing and dispensing system is attained. This unique achievement is realized by creating a single housing or member which comprises a mixing chamber integrally combined with a delivery chamber or tube. The delivery chamber terminates with a portal through which the mixed bone cement is directly dispensed to any desired location.

In order to provide a mixing chamber which can be operated independently of the delivery chamber, the two chambers of the integrated system of the present invention are movable between two alternate positions. In the first position, each chamber is sealed from the other, while in the second position, the two chambers are in direct communication with each other.

By employing the present invention, the two components forming the bone cement are placed in the mixing chamber and intermixed, with complete assurance that no unmixed bone cement will enter the delivery chamber. Complete mixing of the bone cement is assured by providing, in the preferred construction, an integrated counter and display which informs the operator the exact time at which the cement components have been thoroughly intermixed.

Once the two components forming the bone cement are fully intermixed with each other, to provide the desired bone cement product, the integrated, dual chamber system of the present invention is moved from its first sealed position to its second open position, enabling the fully mixed bone cement to be transferred from the mixing chamber directly into the delivery chamber. When desired and under the complete control of the operator, the mixed bone cement is advanced through the delivery chamber to a delivery portal, formed at the terminating end thereof. Then, the fully intermixed bone cement is dispensed through the portal directly to the desired location where the product is to be used.

In the preferred construction of the present invention, the bone cement is transferred through the system to the delivery portal regardless of the position or orientation of the system. In this way, assurance is provided that fully mixed bone cement is delivered to the desired site regardless of the patient's position or the orientation of the bone into which the cement is being dispensed.

One of the principal components of the fully integrated bone cement mixing and delivering system of the present invention is an elongated, multi-component shaft member extending through both the mixing chamber and the delivery chamber of the present invention. Although this elongated shaft member may be formed from a single component, the preferred construction employs at least two components interconnected with each other. In the preferred construction, the shaft member comprises a mixing portion which incorporates a plurality of mixing blades and a movement controlling portion which is preferably formed as a helical shaped auger or helical shaped, radially extending screw thread member.

By employing an elongated, multi-component shaft member which axially extends through both the mixing chamber and the delivery chamber, the mixing portion thereof provides the desired components to cooperate with the walls of the mixing chamber to fully intermix the liquid and powder until the desired bone cement is formed. Once the bone cement has been fully prepared, which information is automatically provided to the user by the rotation counter means, the two cooperating chambers are moved from their first sealed position into their second communicating position, allowing the bone cement to move from the mixing chamber to the delivery chamber.

By rotating the radially extending, substantially continuous, ramped, helical coil or screw thread member of the shaft member in cooperating relationship with the inside wall of the delivery chamber, the fully intermixed bone cement is advanced through the delivery chamber. In addition, the helical, ramped auger or screw threads also extend into the base of the mixing chamber, thereby assuring complete transfer of the mixed bone cement from the mixing chamber to the delivery chamber or tube. Due to the pitch angles employed for these components, the cement is controllably advanced with the mixing/delivery system in any typical orientation or position. The auger also compresses or squeezes the bone cement during the movement through the delivery tube or chamber thereby eliminating substantially all air pockets while also dispensing the material under pressure.

As a result, all of the fully intermixed bone cement is quickly and easily, controllably advanced from the mixing chamber through the delivery chamber to the outlet portal of the delivery chamber. In addition, the movement of the bone cement through the delivery chamber is fully controlled by the rotation of the spiral shaped thread member. Furthermore, the mixing/delivery system of this invention delivers the mixed bone cement at an increased pressure level, thereby assuring that the cement is forced into any cavities or interstices that may exist in the bone being repaired.

By employing the fully integrated, mixing/delivery system of the present invention, the two components forming the bone cement are quickly and easily intermixed and, once the mixture has been formed, automatically fed and delivered to a portal for being controllably advanced to the precisely desired site for its use. In addition, in the preferred embodiment, the radially-extending, ramped, helical-shaped auger/screw thread member is formed to cooperate with the inside wall of the delivery chamber to compress the bone cement as the cement is advanced through the delivery chamber. As a result, any air bubbles or air pockets contained in the mixed cement are broken or eliminated, thereby producing a cement product virtually free of any unwanted air and with adequate pressure to assure complete bonding with the bone material.

By employing the present invention, all of the difficulties and drawbacks found in prior art systems are completely eliminated along with the prior art requirement that the mixed bone cement be manually transferred from a mixing chamber to a delivery component. By achieving a single, fully integrated, mixing/delivering system, user exposure to the mixed bone cement is eliminated and all of the problems encountered with air being entrapped in the mixed bone cement as the bone cement is transferred from the mixing vessel into the delivery means are completely eliminated.

The mixing/delivery system of the present invention is also constructed for being compatible with all types of bone cement. As a result, pre-mixed bone cement or two-component bone cement can be employed with this invention. Furthermore, the system of this invention is equally effective with all viscosity bone cements, thereby enabling a single system to be employed for any bone cement, ranging from low viscosity cements to high viscosity cements. In addition, vacuum may be used, if desired, thereby further expanding the range of products with which the present invention can be employed.

The invention accordingly comprises the features of construction, combinations of elements, and arrangement of parts which will be exemplified in the constructions hereinafter set forth, and the scope of the invention will be indicated in the claims.

THE DRAWINGS

For a fuller understanding of the nature and objects of the present invention, reference should be had to the following detailed description taken in connection with the accompanying drawings, in which:

FIG. 7 is an exploded perspective view, partially in cross-section, depicting an alternate embodiment of the integrated, mixing and delivery system of the present invention;

FIG. 12 is an exploded perspective view, partially in cross section, depicting a still further alternate embodiment of the integrated, mixing and delivery system of the present invention;

FIG. 13 is a cross-sectional side elevation view of the embodiment of mixing and delivery system of FIG. 12 depicted in its first position;

FIG. 14 is a cross-sectional side elevation view of the embodiment of the mixing and delivery system of FIG. 13 depicted in its second position;

FIG. 15 is a cross-sectional view taken along line 15—15 of FIG. 13;

FIG. 16 is a cross-sectional view taken along line 16—16 of FIG. 14, depicting the integrated mixing and delivery system of the present invention in its second position;

FIG. 17 is a side elevation view of the integrated mixing and delivery system of FIGS. 12–16 shown in its second position;

FIG. 18 is a side elevation view of the mixing and delivery system of FIGS. 7–11 shown its second position;

DETAILED DESCRIPTION

Figure 1:
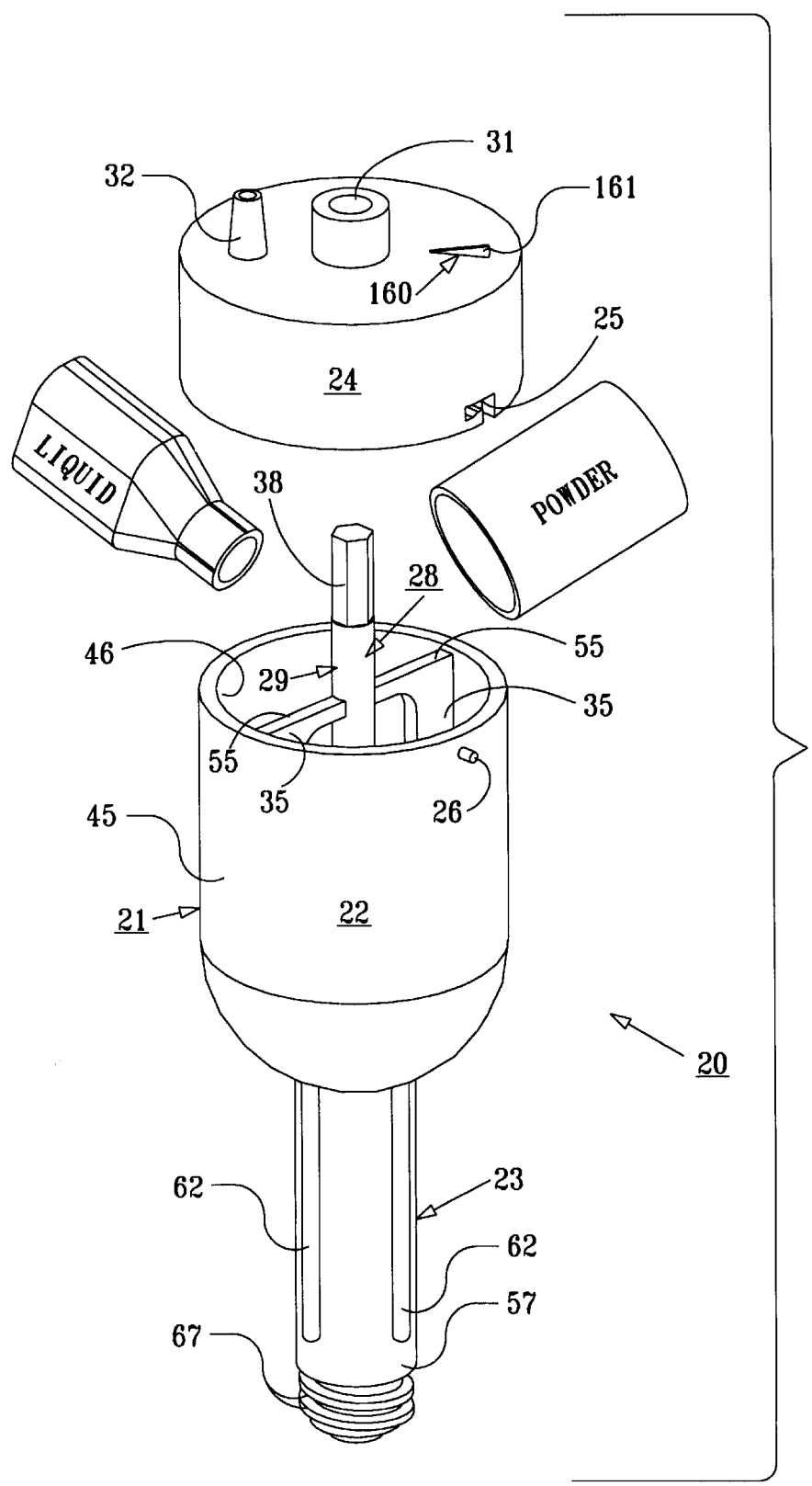
FIG. 1 is a partially exploded perspective view of one embodiment of the integrated mixing and delivery system of the present invention depicted with the two components forming the bone cement being added thereto.

By referring to FIGS. 1–24, along with the following detailed disclosure, the construction and operation of several alternate embodiments of the fully integrated bone cement mixing and delivering system of the present invention can best be understood. Although several alternate embodiments are fully disclosed herein, it is understood that further alternate embodiments can be made without departing from the scope of the present invention. Consequently, the embodiments detailed herein are presented for exemplary purposes only, and are not intended to limit the scope of the present invention.

In FIGS. 1–5, the overall construction of one embodiment of integrated mixing/delivery system 20 of the present invention is fully depicted. In this embodiment, integrated mixing/delivery system 20 comprises an integrated housing 21 which incorporates a mixing chamber 22 and a delivery tube 23 integrally interconnected with each other. In addition, integrated mixing/delivery system 20 also comprises a cover 24 which is removably mountable to mixing chamber 22.

In the preferred construction, cover 24 incorporates a plurality of slots 25 formed about an outer peripheral surface thereof, with each slot 25 cooperating with a raised pin member 26 extending from the outer surface of chamber 22. In this way, cover 24 is easily locked in position, peripherally surrounding and securely closing mixing vessel 22, whenever desired. By positioning slots 25 with cooperating pin members 26 and rotating cover member 22 relative to chamber 22, pin 26 is advanced into locked engagement with slot 25. Whenever cover 22 is to be removed from chamber 22, the process is reversed, thereby enabling cover 22 to be easily removed therefrom.

The overall construction of integrated, mixing/delivering system 20 of the present invention is completed by incorporating elongated, multi-component shaft member 28 which comprises mixing portion 29 and movement controlling portion 30. Although shaft member 28 may be constructed as a single component, it has been found that the preferred construction is to form shaft member 28 from at least two separate and distinct sections, each of which are integrally interconnected to each other. However, if desired, three or more sections can be employed, as well as a single elongated component, without departing from the scope of this invention.

Furthermore, cover 24 incorporates a centrally disposed aperture 31 constructed for enabling shaft member 28 to extend therethrough and be rotationally driven from outside of mixing vessel 22. In order to prevent unwanted leakage, the dimensions of aperture 31 and shaft member 28 are maintained in close relationship to each other.

As discussed above, mixing/delivery system 20 of the present invention may be employed when connected to a vacuum source, in order to further enhance the removal of all air bubbles or air pockets. In addition, certain types of bone cement are more likely to develop air pockets during the mixing and delivery system and, as a result, are best employed with mixing/delivery system 20 connected to a vacuum source. In order to enable mixing/delivery system 20 of the present invention to be quickly and easily interconnected to a vacuum source, cover 24 incorporates a fitting 32 constructed for enabling a vacuum source to be directly connected to mixing chamber 22 to provide the desired removal of air from the bone cement being mixed therein. Of course, if a vacuum source is not required, vacuum fitting 32 would be sealed, if desired, so as to enable the bone cement to be intermixed without being exposed to vacuum conditions.

Another feature incorporated into the mixing/delivery system of the present invention is the incorporation of indictor means 160 which provides the operator with a positive indication that the bone cement is completely mixed and ready for delivery. The preferred construction for indicator means 160 is fully detailed below, with FIG. 1 depicting a window member 161 through which a positive, visual indicator is easily observed which provides the operator with visual notice of the progress being made during the mixing cycle. Once the bone cement has been fully and completely intermixed and is ready for delivery, an easily observable indication is displayed through window 161 of indicator means 160.

In the preferred construction, mixing portion 29 of elongated, multi-component shaft member 28 comprises an elongated, rod member 34 and at least two mixing blades 35,35 integrally attached to rod member 34 and radially extending therefrom. As is more fully detailed below, mixing blades 35,35 are preferably formed with an arcuately curved shape, and with an outer edge constructed having a size and shape that provides a cooperative relationship with mixing chamber 21.

Although mixing blades 35,35 may be constructed without an arcuate curved shape, comprising substantially flat, planar blade members, the preferred construction of mixing blades 35,35 comprise an arcuately curved shape which ranges between about 45° and 360°. As is more fully detailed below, the preferred arcuate curve formed in blades 35,35 ranges between about 90° and 180°.

In the preferred embodiment, mixing portion 29 comprises post receiving socket 36 formed at the distal end of rod member 34, with socket 36 comprising a size and shape constructed for secure, locked, driving interengagement with post 37 of movement controlling portion 30. In the preferred embodiment, post receiving socket 36 comprises a generally square or rectangular shape, dimensioned for receiving, secure, locked interengagement with square or rectangular shaped post 37 of movement controlling portion 30.

The construction of mixing portion 29 of shaft member 28 is preferably completed by forming terminating end 38 of rod member 34 for being received and locked in interengagement with drive means 39 (FIG. 3), employed for rotating shaft member 28 when desired. As further discussed herein, when desired, shaft member 28 is continuously, controllably rotated in order to enable blade members 35,35 to cooperate with the inside walls of mixing chamber 22 and fully mix the two components forming the desired bone cement.

In addition, in order to provide the desired controlled movement of the mixed cement through delivery tube 23, as well as its delivery under pressure, movement controlling portion 30 is rotated in cooperating relationship with the inside walls of delivery tube 23. This rotational movement is provided under the complete control of the user by employing drive means 39 securely engaged with terminating end 38 of mixing portion 29 of shaft member 28.

Figures 3, 3A:
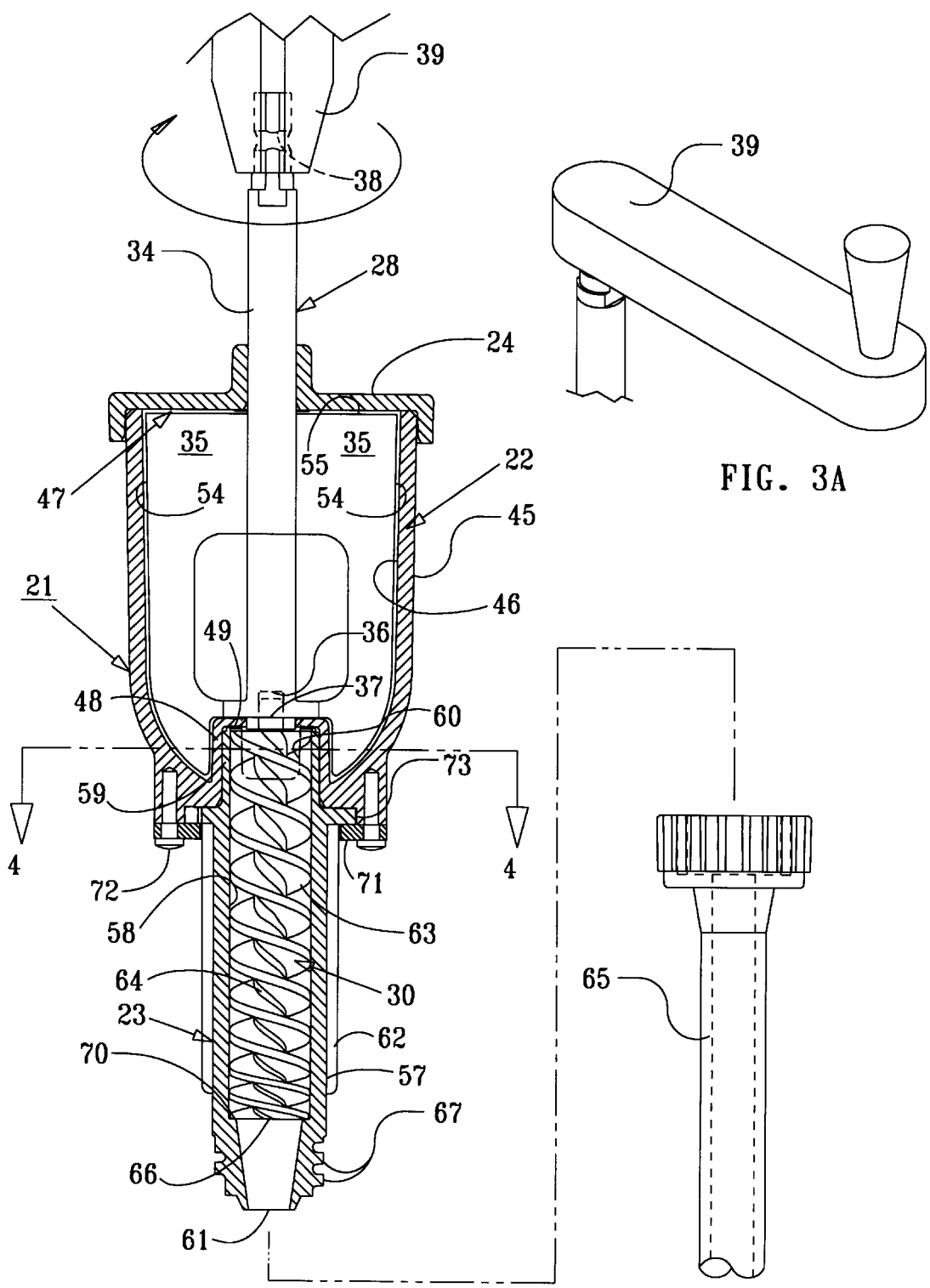
FIG. 3 is a cross-sectional side elevation view depicting the integrated mixing and delivery system of the present invention fully assembled.
FIG. 3A is a perspective view of alternate drive means for rotating the shaft means of the integrated bone cement mixing and dispensing system.

In the preferred implementation of the present invention, drive means 39 for elongated, multi-component shaft member 28 comprises a rotatable drill member, as depicted in FIG. 3. If desired, however, any alternate drive means can be employed without departing from the scope of the invention, such as manual handle drive shown in FIG. 3A.

In the preferred embodiment, drive means 39 is capable of rotating shaft member 28 with sufficient speed to assure the mixing of the components forming the bone cement and the controlled delivery of the mixed bone cement through delivery tube 23. In this way, assurance is provided that the two-part bone cement is completely intermixed and, when completed, controllably advanced through delivery tube 23 to the outlet portal thereof, with the cement being delivered under pressure, to assure secure bonded engagement in the desired location.

In the embodiment depicted in FIGS. 1–5, mixing chamber 22 is formed in a substantially U-shape, comprising outer wall 45 and inner wall 46. In addition, mixing chamber 22 comprises an enlarged, open entry zone 47 formed at the top of the substantially U-shaped chamber 22, and an upstanding collar 48 formed at the base of U-shaped chamber 22.

In the preferred construction, upstanding collar 48 comprises an upstanding, substantially circular shape, incorporating a central aperture 49 for receiving elongated, multi-component shaft member 28, and two enlarged side portal zone 50 formed in the sides of upstanding collar 48 substantially diametrically opposed from each other. As is more fully detailed below, portal zones 50 provide the communication between mixing chamber 22 and delivery tube 23.

As briefly discussed above, each of the two mixing blades, 35,35 are mounted to rod member 34 of elongated, multi-component shaft member 28 cooperating therewith to form mixing portion 29. In this embodiment, each mixing blade 35 comprises an outer edge 54 which is dimensioned to conform with the axial or longitudinal, curved shape of inside wall 46 of U-shaped mixing chamber 22. In addition, outer edge 54 of each mixing blade 35 is dimensioned for being in juxtaposed, spaced, aligned, close relationship with inside wall 46 of mixing chamber 22 in order to assure that the components forming the bone cement are efficiently and easily contacted and completely intermixed by the rotational movement of blade members 35,35 relative to inside wall 46 of mixing chamber 22.

In addition, each blade member 35 also comprises an overall axial length substantially equivalent to the axial length of inside wall 46 of mixing chamber 22. Preferably, top edge 55 of each mixing blade 35 radially extends outwardly from rod member 34 in juxtaposed, spaced cooperating relationship with the inside surface of cover 24. As a result, complete intermixing of the components forming the bone cement is assured.

In this embodiment, delivery tube 23 comprises an elongated, generally cylindrical shape defined by outer surface 57 and inner surface 58. In addition, the end of delivery tube 23, which cooperates with mixing chamber 22, comprises an upstanding, substantially cylindrically shaped wall 59 dimensioned for retained inserted engagement within collar 48 of mixing chamber 22.

In addition, cutout zones 60 are formed in upstanding wall 59 forming a communicating portal zone between the interior of mixing chamber 22 and the interior of delivery tube 23. In the preferred construction, two cutout zones 60 are formed in wall 59 positioned in juxtaposed, spaced diametrically opposed locations thereof. Cutout zones 60 are constructed for cooperating relationship with portal zones 50 of collar 48 in order to provide at least two positions relative thereto. In one position, the interior of mixing chamber 22 is completely sealed from the interior of delivery tube 23, while in the second, alternate position, the two interior zones are in communication with each other.

In the preferred construction of this embodiment of the present invention, delivery tube 23 is constructed with a plurality of ribs 62 formed on outer surface 57 of delivery tube 23. Preferably, ribs 62 are formed as longitudinally extending ribs positioned in juxtaposed spaced relationship to each other on outer surface 57. Although not required, ribs 62 are preferred in order to assist the user in arcuately rotating delivery tube 23 relative to mixing vessel 22 whenever mixing/delivery system 20 is moved from its first position into its second position.

Furthermore, in the preferred construction, delivery tube 23 incorporates a ledge 70 at the juncture between inside wall 58 and outlet portal 61. As best seen in FIG. 3, ledge 70 is constructed for cooperating relationship with distal end 66 of movement controlling portion 30 for receiving and securely positioning distal end 66 in the precisely desired manner wherein movement controlling portion 30 is capable of continuously rotating, while enabling the intermixed bone cement to be transferred through delivery tube 23 to outlet portal 61 under the desired pressure level.

In order to best understand the cooperating relationship of delivery tube 23 to mixing chamber 22 and the two alternate positions provided by mixing/delivery system 20 of the present invention, reference should be made to FIGS. 2–5 along with the following detailed disclosure. As shown therein, when delivery tube 23 and mixing chamber 22 are fully assembled, upstanding wall 59 is telescopically inserted and cooperatively received within collar 48 of mixing chamber 22.

Figure 4:
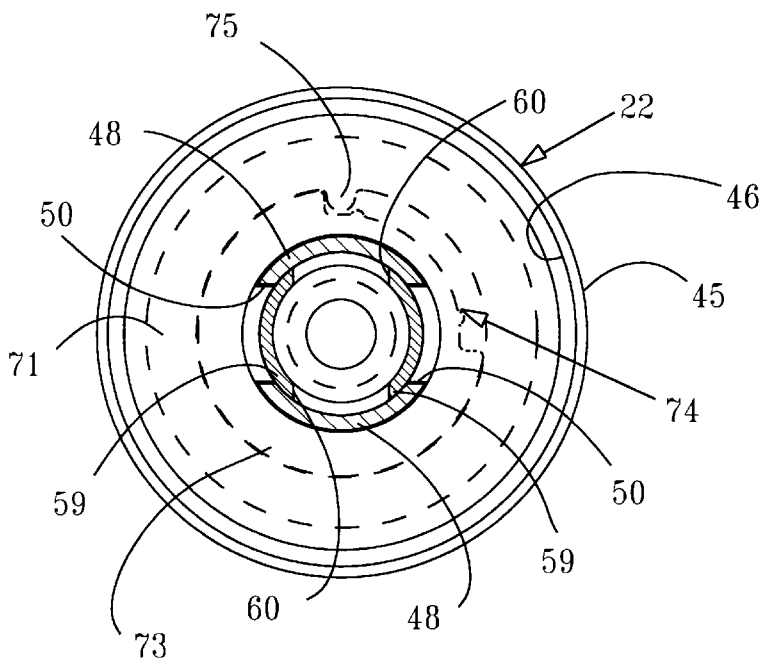
FIG. 4 is a cross-sectional view of the integrated mixing and delivery system of the present invention taken along line 4—4 of FIG. 3, showing the system in its first position.

In the first cooperative position, depicted in FIG. 4, mixing chamber 22 is sealed from delivery tube 23. When in this position, upstanding wall 59 of delivery tube 23 is in juxtaposed, spaced, blocking relationship with portal zones 50,50 of collar 48. As a result, when mixing delivery system 20 of the present invention is maintained in this first position, the components forming the bone cement can be inserted into mixing chamber 22 and completely intermixed without fear that any partially mixed cement will be transferred from mixing chamber 22 to delivery tube 23.

Figure 5:
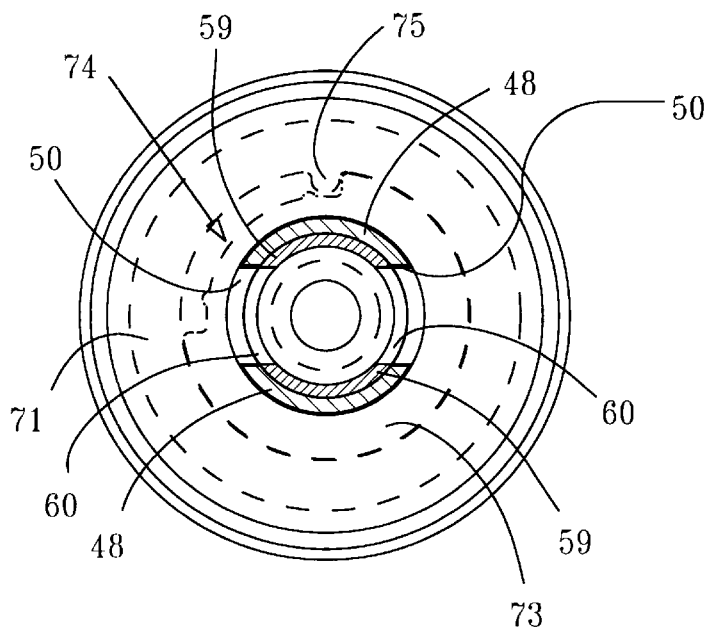
FIG. 5 is a cross-sectional view, similar to FIG. 4, showing the integrated mixing and delivery system of the present invention in its second position.

In the second position of mixing/delivery system 20, depicted in FIG. 5, the interior of mixing chamber 22 is in direct communication with the interior of delivery tube 23. In this position, delivery tube 23 is arcuately rotated relative to mixing chamber 22, causing cutout zones 60,60 of upstanding wall 59 to be aligned with portal zones 50,50 of collar 48. As a result, when mixing/delivery system 20 is in this position, the fully mixed bone cement is capable of passing through portal zones 50,50 and cutout zones 60,60 to be completely transferred from mixing chamber 22 into delivery tube 23.

The construction of this embodiment of mixing/delivery system 20 is completed by securely affixing plate 71 to the base of mixing chamber 22 by employing screw means 72. Preferably, mixing tube 23 incorporates a radially extending cam-ring 73 which is sandwiched between mixing chamber 22 and plate 71 when plate 71 is secured in position.

Figure 2:
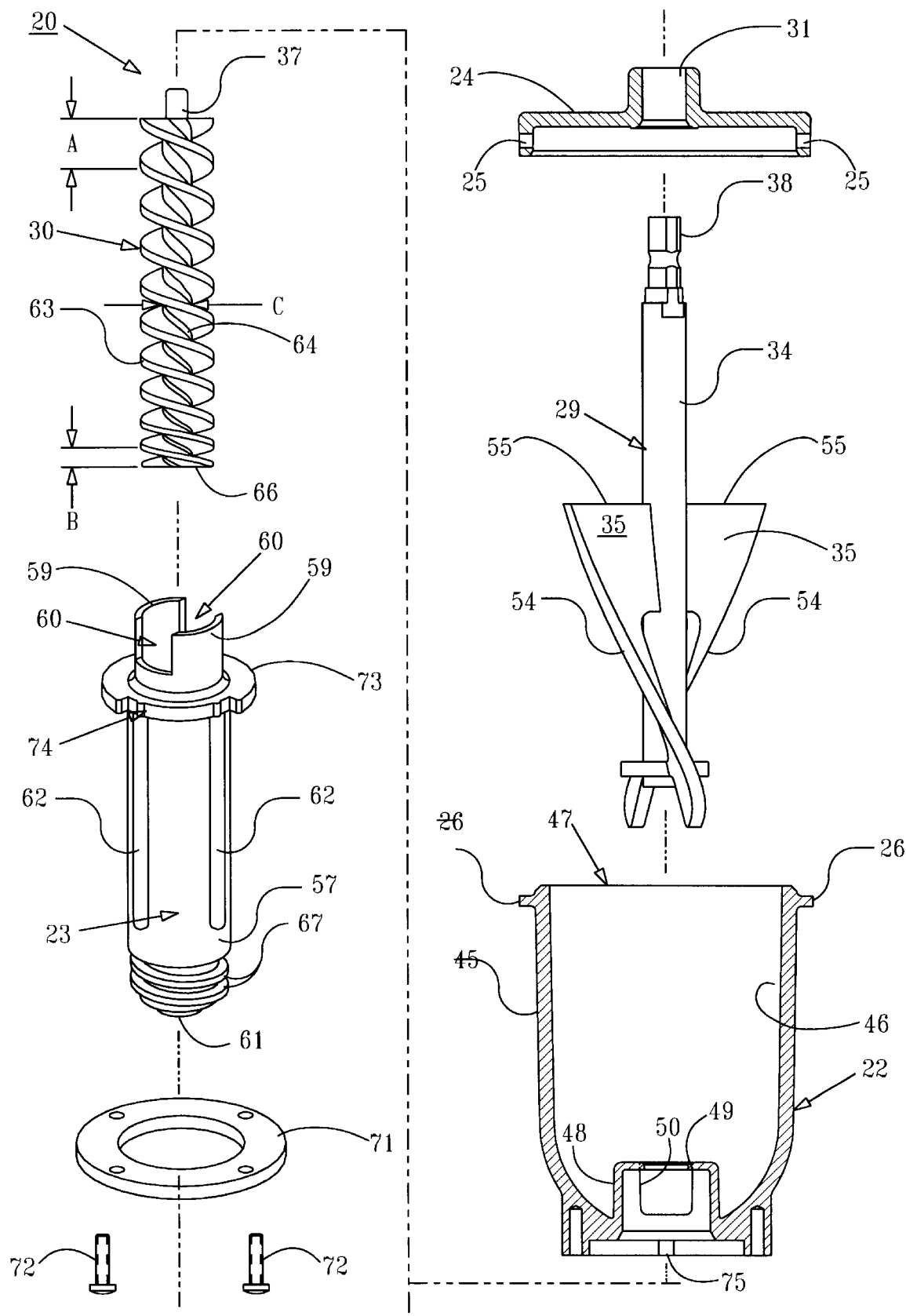
FIG. 2 is an exploded perspective view, partially in cross-section, of the integrated mixing and delivery system of the present invention detailing the mixing and delivery system of the present invention.

As best seen in FIGS. 2, 4 and 5, cam ring 73 incorporates a cam surface 74 constructed for defining the two alternate positions of delivery tube 23 relative to mixing chamber 22, as well as the intermediate travel positions therebetween. By employing a cam post 75, mounted either to mixing vessel 22 or plate 71, the two alternate positions of delivery tube 23 relative to mixing vessel 22 are defined and easily attained, while assuring no further movement beyond these two alternate positions.

By employing this construction, the first position, as depicted in FIG. 4, is attained when cam post 75 is in abutting contact with one end of cam surface 74 of cam ring 73. By arcuately rotating delivery tube 23 relative to mixing chamber 22, cam surface 74 is moved relative to cam post 75 a distance of about 90°, until the opposed end of cam surface 74 is brought into abutting contact with cam post 75. Once in this position, the second position of mixing/delivery system 20 is attained.

By employing this construction, the operator is capable of completely mixing the two components forming the bone cement with the assurance that the bone cement is completely intermixed prior to any cement composition being transferred to delivery tube 23. Once the bone cement is fully prepared by complete intermixture, mixing/delivery system 20 is moved from its first position to its second position, enabling the completely intermixed bone cement to be transferred from mixing chamber 22 to delivery tube 23.

As is apparent from the preceding detailed disclosure, the movement of the fully mixed bone cement from mixing chamber 22 to delivery tube 23 is achieved in a completely sealed environment, with cover 24 remaining in place, sealing mixing chamber 22 from exposure to the ambient air. As a result, none of the difficulties and drawbacks found with prior art systems are encountered, and automatic, safe, convenient, full-proof transfer of the bone cement from the mixing chamber to the delivery chamber is realized, without exposing the operator to the noxious, offensive odor associated with the bone cement.

In order to assure that the fully mixed bone cement is transferred through delivery tube 23 to outlet portal 61, formed at the distal end of delivery tube 23, movement control portion 30 of elongated, multi-component shaft member 28 is employed. In the embodiment depicted in FIGS. 1–5, movement controlling portion 30 comprises a continuous, radially extending, ramped, helical or spiral shaped auger or screw thread member 63. As shown in FIGS. 2 and 3, continuous, ramped, helical or spiral shaped auger/screw thread member 63 radially extends outwardly from elongated, supporting rod member 64. In this embodiment, rod member 64 comprises a substantially uniform diameter "C" throughout its length.

As discussed above, one end of rod member 64 of movement controlling portion 30 is formed with substantially square shaped or rectangular shaped post 37, constructed for being inserted through aperture 49 of collar 48 of mixing chamber 22 and being securely, lockingly and drivingly engaged with post receiving socket 36 of rod member 34 of mixing portion 29. In addition, opposed end 66 of rod member 64 is preferably formed with a substantially flat surface constructed for nested, rotational engagement with edge 70 of delivery tube 23. In this way, the rotational movement imparted to multi-component shaft member 28 by drive means 39 causes mixing blades 35 to rotate about the axes of rod member 29 while simultaneously causing helical or spiral thread member 63 to rotate about the central axis of rod member 64.

Continuous, ramped, radially extending, helical or spiral shaped auger/screw thread member 63 is mounted to rod member 64 with an angular pitch which assures that a plurality of convolutions are formed along the length of rod member 64. In this way, the desired controlled movement of the bone cement through delivery tube 23 is provided.

In order to assure complete, controlled movement of the mixed bone cement from mixing chamber 22 through delivery tube 23, helical or spiral shaped screw thread member 63 comprises a diameter slightly less but dimensionally similar to the diameter of inner wall 58 of delivery tube 23. In this way, assurance is provided that movement controlling member 30 is free to rotate within delivery tube 23 while being in close, juxtaposed, spaced, cooperating relationship with the inside wall thereof. As a result, all of the mixed bone cement is controllably advanced through the interior of delivery tube 23, with maximum compression of the bone cement being attained as well as pressure build-up for forcing the bone cement into the desired bone structure.

In order to enhance the compression of the bone cement during its travel through tube 23, the preferred embodiment of movement controlling portion 30 is formed with the spacing between each adjacent thread or convolution of continuous screw thread members 63 decreasing as the thread members 63 advance from post 37 to the opposed, distal, terminating end 66 of movement controlling portion 30. Although any desired spaced distance can be employed between adjacent threads or convolutions to attain the benefit derived from this invention, it has been found that the spacing preferably ranges between about 1.25 and 0.10 inches. It has also been found that different bone cement viscosities are preferably advanced using different thread spacings. Generally, bone cement having a low viscosity preferably employs a controlling portion 30 wherein the spacing between adjacent threads or convolutions ranges between about 0.25 and 0.10 inches. In addition, bone cement having a high viscosity preferably employs a controlling portion 30 having a spacing between adjacent threads or convolutions ranging between about 1.25 and 0.185 inches.

In order to best understand this preferred construction, reference should be made to FIG. 2. As shown therein, the distance defined by spacing "A", which is adjacent post 37, is greater than the distance defined by spacing "B", located adjacent distal end 66 of controlling portion 30. Preferably, the distances employed fall within the ranges detailed above. In addition, the distance between the intermediate threads or convolutions continuously decreases, consistent with the dimensions of spacings "A" and "B".

By constructing screw thread members 63 with the variable spacing detailed above, a variable pitch is imparted to screw thread members 63 throughout the length of movement controlling portion 30. By employing this variable pitch construction, it has been found that the mixed bone cement is not only controllably advanced through delivery tube 23, but is more effectively compressed and squeezed during the axial transfer of the bone cement through delivery tube 23. Furthermore, this construction is able to force the mixed bone cement out of portal 61 under pressure, which assures complete filling of all cavities in the bone.

As a result of this construction, controlled compression of the bone cement is achieved during its advance through tube 23, causing any air entrapped in the mixed bone cement to be forced out automatically by the delivery process. In this way, the bone cement delivered through portal 61 of delivery tube 23 is substantially free of entrapped air, attaining a bone cement having all of the qualities and inherent characteristics desired by the surgeon.

In most applications wherein mixing/delivery system 20 is employed, outlet portal 61 of delivery tube 23 is positioned in direct association with the particular bone cavity or joint into which the cement is to be dispensed. As a result, by activating drive means 29, after the bone cement has been fully mixed and mixing/delivery system 20 has been rotated into its second, chamber communicating position, the fully mixed bone cement is advanced through delivery tube 23 directly to the site desired under pressure for its use.

In some applications, outlet portal 61 is unable to reach the desired site. In order to accommodate these instances, an extension tube 65, shown in FIG. 3, is employed to deliver the mixed bone cement to more remote locations or locations where delivery tube 23 cannot be easily positioned.

In order to assure ease of mounting of extension tube 65 to the terminating, distal end of delivery tube 23, in a peripherally surrounding and cooperating manner with outlet portal 61, the distal end of delivery tube 23 incorporates thread means 67 formed thereon. In addition, extension tube 65 incorporates cooperating thread means formed at its proximal end, thereby enabling extension tube 65 to be quickly and easily threadedly engaged to thread means 67 of the distal end of delivery tube 23. Once mounted in position, the activation of drive means 39 causes the mixed bone cement to be advanced through delivery tube 23, out of portal 61 and through the interior of extension tube 65, until the fully intermixed bone cement is delivered to the precisely desired surgical site.

In addition, the system of this invention forces the mixed bone cement through portal 61 and tube 65, if employed, under pressure to enable the surgeon to use standard bone filling techniques to fill all cavities and interstices in the bone with cement, thereby providing secure bonded engagement. Typically, after filing the bone canal with cement, mixing/delivery system 20 is sealed against the opening of the bone canal. Then, by rotating movement controlling portion 30, pressure is created which insures the cement creates a good interlock between cement and bone. The pressurization increases the subsequent strength of the bone cement and improves the quality of the mechanical interlock between cement and bone by forcing the cement into irregularities in the bone's surface.

Figure 6:
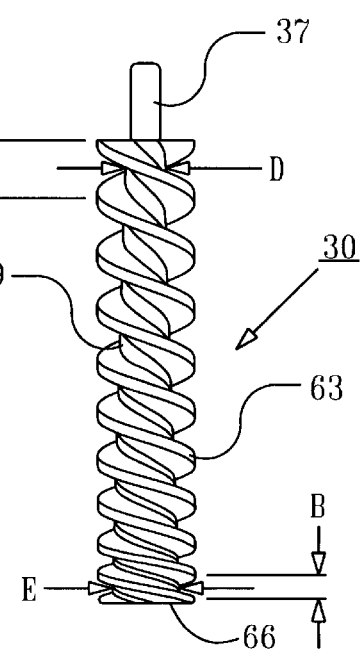
FIG. 6 is a side elevation view detailing an alternate embodiment of the movement control means forming a component of the integrated mixing and delivery system of the present invention.
Figure 8:
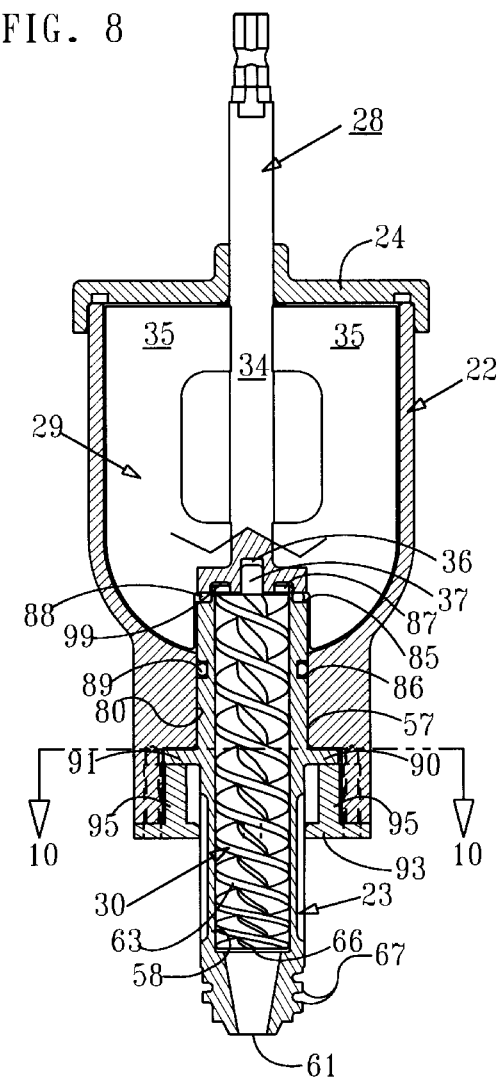
FIG. 8 is a cross-sectional, side elevation view, of the fully assembled mixing and delivery system of FIG. 7 shown in its first position.

In FIG. 6, an alternate embodiment for movement controlling portion 30 is depicted. In this embodiment, movement controlling portion 30 comprises an overall shape and construction similar to the construction detailed above. These similarities are evident from the construction depicted in FIG. 6, as well as the reference indices employed. In this regard, reference indicia discussed above and shown in FIG. 6 has equal applicability to the embodiment of FIG. 6.

In this alternate construction, one principal variation incorporated in movement controlling portion 30 is the construction thereof with a rod member 69 having a tapered diameter. As depicted in FIG. 6, the diameter of rod member 69 increases as one advances from the proximal end of rod member 69, adjacent post 37, to opposed, terminating distal end 66.

As shown in FIG. 6, the diameter of tapered rod member 69 varies from a diameter "D", adjacent post 37, to a diameter "E", adjacent distal end 66. Although any desired diameter range can be employed to attain the benefit provided by this embodiment, it has been found that the preferred diameter for tapered rod member 69 ranges between about 0.18 inches and 0.50 inches. In the preferred construction as depicted in FIG. 6, diameter "D" ranges between about 0.18 inches and 0.30 inches, while diameter "E" ranges between about 0.38 inches and 0.50 inches.

By employing this tapered, diameter construction for rod member 69, with continuous, ramped, radially extending, helical or spiral shaped auger or screw thread member 63 mounted thereto, a construction is attained wherein the distal end of delivery tube 23 comprises an overall area which is smaller than the area provided by the embodiment depicted in FIG. 3. As a result, further compression of the mixed bone cement is attained and added assurance is provided that all entrapped air is removed and additional exit pressure is generated. Furthermore, by employing this construction, added strength and rigidity is imparted to movement controlling portion 30, particularly in the area directly adjacent outlet portal 61 where added pressure is imparted to the screw thread member, due to the proximity of the thread members to each other.

Figure 19:
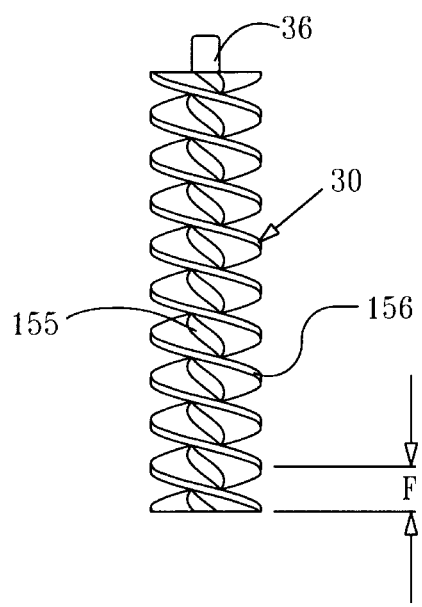
FIG. 19 is a side elevation view detailing a further alternate embodiment of the movement controlling means forming a component of the integrated mixing and delivery system of the present invention.
Figure 20:
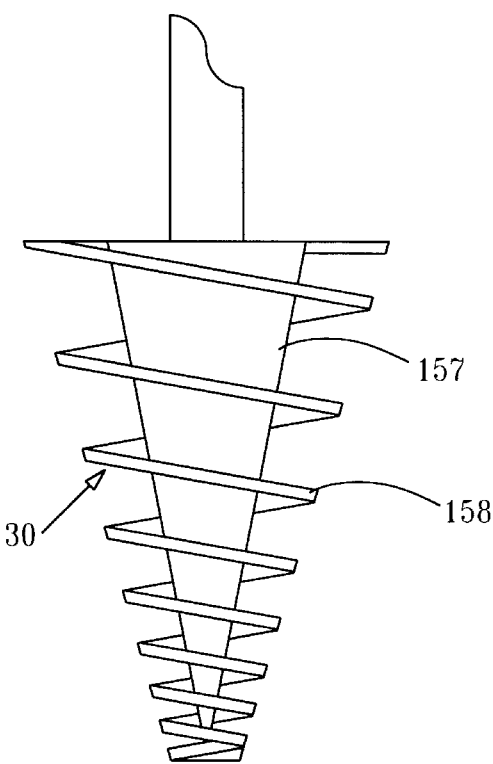
FIG. 20 is a side elevation view detailing a still further alternate embodiment of the movement controlling means forming a component of the integrated mixing and delivery system of the present invention.

By referring to FIGS. 19 and 20, two further alternate embodiments for movement controlling portion 30 of the present invention are depicted. In the embodiment depicted in FIG. 19, movement controlling portion 30 comprises a rod member 155 which may comprise either a uniform diameter throughout its length or may be tapered, as detailed above. Mounted to rod member 155 is continuous, ramped, radially extending, helically shaped auger or screw thread member 156 which is constructed in this embodiment with spaced distance "F" between each adjacent thread member comprising a substantially equivalent distance throughout the entire length of rod member 155. Depending upon a particular type of bone cement being employed, movement controlling portion 30 with a uniform pitch screw thread member 156 may be effectively employed.

In the embodiment depicted in FIG. 20, movement controlling portion 30 comprises a rod member 157 which is tapered in the opposite direction of movement controlling portion 30 of FIG. 6. In this embodiment, the largest diameter of rod member 157 is formed near the juncture with mixing chamber 22 while the smallest diameter thereof is formed at the distal end of movement controlling portion 30. Mounted to rod member 157 is a continuous, ramped, radially extending, helical-shaped auger or screw thread member 158 which may be formed with either a variable spacing between adjacent thread members or a uniform spacing, as detailed above. However, in the preferred construction, screw thread member 63 would be constructed using the variable pitch configuration thoroughly detailed above.

By employing the funnel shaped rod member 157 for movement controlling portion 30, the tube member with which this construction would be associated would be formed in a substantially complimentary funnel shape. In this construction, it has been found that maximum pressure and bone cement squeezing is attained due to the substantially reduced area near the distal end of the delivery tube. Consequently, for certain viscosities of bone cement, this construction provides highly effective results.

In FIGS. 7–11, a second, alternate embodiment of a fully integrated, bone cement mixing and delivering system 20 of the present invention is fully detailed. For convenience and ease of understanding, these drawings, and the following detailed disclosure, employ similar reference numerals for similar structural components. As a result, it is to be understood that in addition to the following detailed disclosure regarding the embodiment of FIGS. 7–11, the foregoing detailed disclosure relating to the particular similar structural components is equally applicable to this embodiment and the structure of the components employed therein.

In this embodiment, integrated, mixing/delivery system 20 comprises an integrated housing 21 which incorporates a mixing chamber 22 and a delivery tube 23 integrally interconnected with mixing chamber 22. In addition, integrated mixing/delivery system 20 also incorporates a cover 24 which is removably mountable to mixing chamber 22 in the manner detailed above.

In this embodiment, cover 24 preferably incorporates a circular notch 76 formed in the underside of cover 24 with notch 76 comprising a diameter generally equivalent to the diameter of the cylindrical wall forming mixing chamber 22. In addition, O-ring 77 is also incorporated into this embodiment, for being positioned within notch 76. In this way, when cover 24 is securely affixed to mixing chamber 22, a sealing zone is established by O-ring 77 and notch 76 in order to prevent any unwanted seepage of bone cement from mixing chamber 22 during the mixing process.

As with the embodiment detailed above, this embodiment of the integrated, mixing/delivery system 20 incorporates elongated, multi-component shaft member 28 which comprises mixing portion 29 and movement controlling portion 30. As detailed above, mixing portion 29 of elongated, multi-component shaft member 28 comprises an elongated rod member 34 and at least two mixing blades 35,35 integrally attached to rod member 34 and radially extending therefrom. In addition, in the preferred construction, mixing blades 35,35 are formed in an arcuately curved shape, with outer edge 54 having a size and shape constructed for cooperative relationship with inside wall 46 of mixing chamber 22.

In this embodiment, the preferred construction of mixing portion 29 and movement controlling portion 30 of mixing/delivery system 20 is substantially identical to the construction detailed above. As shown in FIGS. 7–11, movement controlling portion 30 comprises continuous, ramped, radially extending helical-shaped auger or screw thread member 63 extending from substantially uniform diameter rod member 64. However, if desired, tapered diameter rod member 69 can be employed with equal efficacy and effect as well as the further alternate structures detailed above.

The principal differences between the embodiment depicted in FIGS. 7–11 and the embodiment detailed above and shown in FIGS. 1–5 is found in the construction and cooperative interengagement between mixing chamber 22 and delivery tube 23 to form unitary housing 21. As detailed herein, a further unique construction is employed for providing sealable interengagement between mixing chamber 22 and delivery tube 23, as well as for providing movement between a first sealed position, wherein the interior of mixing chamber 22 is completely sealed from the interior of delivery tube 23, and a second position, wherein these interior zones are in communication with each other. The following disclosure details this additional unique construction, as well as the cooperation with some of the elements detailed above.

In this alternate embodiment, mixing chamber 22 comprises a substantially U-shape, formed by outer wall 45 and inner wall 46. In addition, mixing chamber 22 comprises an enlarged open entry zone 47 formed at the top of substantially U-shaped chamber 22 which is constructed for the cooperative sealing interengagement with cover 24 and sealing O-ring 77.

In this embodiment, the base or lower portion of mixing chamber 22 comprises a substantially circular shaped opening or passageway 80 which extends from the interior of mixing chamber 22 part way toward bottom 82. In addition, mixing chamber 22 incorporates an enlarged open zone 81 which extends from passageway 80 to bottom 82 of mixing chamber 22. Mixing chamber 22 also incorporates a plurality of screw-receiving holes 83 which are preferably positioned in relationship with open zone 81 of mixing chamber 22, with threaded screw-receiving holes 83 being open from bottom 82.

In this embodiment, delivery tube 23 comprises an outer surface 57, an inside surface 58, which defines the interior zone in which movement controlling portion 30 is positioned for cooperative relationship with inside wall 58 in order to controllably move the mixed bone cement therethrough from the interior of mixing chamber 22 through outlet portal 61 of delivery tube 23. Furthermore, outside surface 57 of delivery tube 23 comprises two circular shaped recesses or notches 85 and 86 both of which are formed in cooperating relationship with proximal end-forming flange 87 of delivery tube 23. In addition, O-ring 88 is positioned in notch 85, while O-ring 89 is positioned in notch 86. Finally, substantially mid-way along the length of outer surface 57 of delivery tube 23, a pair of radially extending arms 90 and 91 are positioned.

The diameter of outer wall 57 of the upper portion of delivery tube 23 is constructed for being substantially equivalent to and slightly less than the diameter of aperture 80. In this regard, the diameter of aperture 80 and the diameter of outer wall 57 of the upper portion of delivery tube 23 are dimensioned for cooperative, sliding interengagement, while preventing any unwanted passage or seepage of the bone cement therebetween. In order to assist in preventing any unwanted seepage or passage of bone cement between aperture 80 and outside wall 57 of delivery tube 23, O-ring 88 and 89 are mounted in recesses 85 and 86, effectively sealing the area between these two cooperating components, while still enabling the desired axial sliding movement therebetween.

The construction of this embodiment of mixing/delivery system 20 is completed by mounting collar plate 93 to bottom 82 of mixing vessel 22. Collar plate 93 is constructed for direct mounted affixation to the bottom of mixing chamber 22 by employing screw means 94 which are inserted through receiving apertures in collar plate 93 and securely mounted in screw receiving holes 83 of mixing chamber 22.

In the preferred construction, collar plate 93 comprises two upstanding walls or posts 95,95 which are constructed for being positioned within open zone 81 in cooperating relationship therewith. Posts 95 extend substantially perpendicularly from plate 93 a sufficient distance to provide a space between the end of posts 95,95 and the juncture of aperture 80 and zone 81 with the space being at least equal to the thickness of arms 90 and 91. In this way, arms 90 and 91 are independently retained on one post 95, preventing axial movement of delivery tube 23. However, whenever desired, arms 90 and 91 are rotated away from retained engagement with posts 95, thereby enabling axial movement of arms 90 and 91, along with tube 23.

When this embodiment of mixing/delivery system 20 is fully assembled and placed in the closed position, with the interior of mixing chamber 22 completely independent from the interior of delivery tube 23, radially extending arms 90 and 91 are captured and maintained in position by upstanding posts 95,95 of collar plate 93. When in this position, the upper proximal portion of delivery tube 23 is maintained within aperture 80 of mixing vessel 22, while also extending into the bottom of mixing chamber 22 in peripheral surrounding and sealing relationship with ramped, radially extending helical shaped auger or screw thread member 63 of movement controlling portion 30. As a result, any contact of screw thread member 63 with the bone cement is prevented and all of the bone cement is safely maintained within the interior of mixing chamber 22.

In order to assure secure, seepage-free separation of the bone cement from movement controlling portion 30, O-ring 88 is placed in contacting engagement with the base of rod member 34 of mixing portion 29, while end-forming flange 87 is inserted in groove 99 formed about socket 36. In this way, complete sealing of movement controlling portion 30 from exposure to the bone cement within the interior of mixing chamber 22 is attained, when mixing/delivery chamber 20 is in its first position.

In order to move mixing/delivery system 20 from its first position into its second position, wherein the interior of mixing chamber 22 is in communication with the interior of delivery tube 23, delivery tube 23 is arcuately rotated about its central axis by moving radially extending arms 90 and 91 away from retained engagement on posts 95 until arms 90 and 91 are away from posts 95 and within open zone 81. Once arms 90 and 91 are positioned within open zone 81, delivery tube 23 is capable of axial, telescopic movement, in its entirety, relative to mixing vessel 22.

Once free from posts 95, delivery tube 23 is axially movable downwardly, causing arms 90 and 91 to advance towards bottom 82 of mixing chamber 22. During the axial movement, proximal end-forming flange 87 of delivery tube 23 is moved away from sealing engagement with rod member 34 of mixing portion 29, effectively exposing the proximal end of movement controlling portion 30 to the interior of mixing chamber 22.

Figure 9:
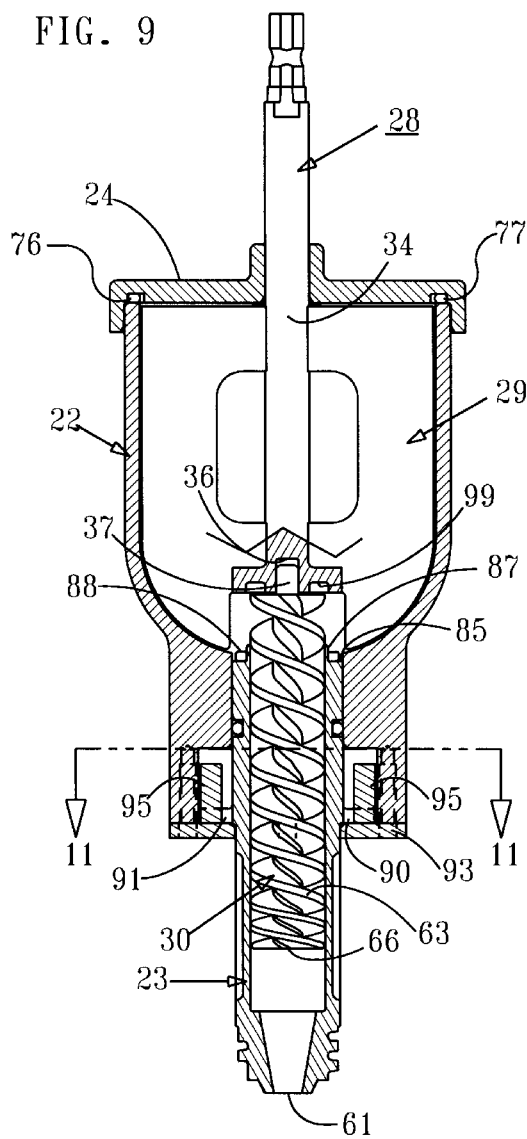
FIG. 9 is a cross-sectional, side elevation view of the embodiment of integrated mixing and delivery system of FIG. 8 shown in its second position.
Figure 10:
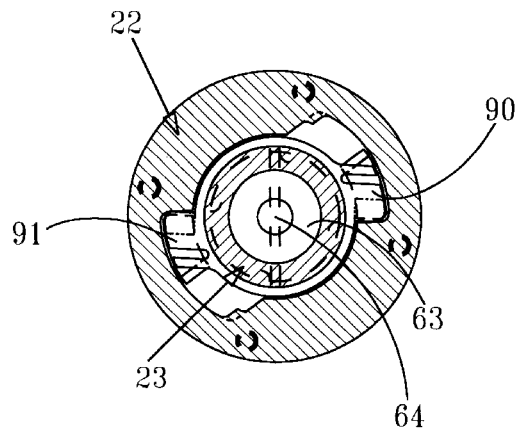
FIG. 10 is a cross-sectional view of the mixing and delivery system of FIG. 8 taken along line 10—10 of FIG. 8.
Figure 11:
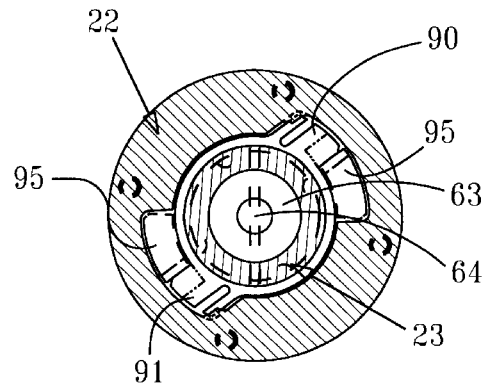
FIG. 11 is a cross-sectional view of the mixing and delivery system of FIG. 9 taken along line 11—11 of FIG. 9.

When axial movement is complete, as clearly depicted in FIG. 9, continuous, ramped, radially extending helical shaped auger or screw thread member 63 is fully exposed to the mixed bone cement contained within mixing chamber 22, enabling the rotation of elongated, multi-component shaft member 28 to effectively advance the mixed bone cement from chamber 22 through delivery tube 23 until the desired mixed bone cement has been transferred through delivery tube 23 to outlet portal 61.

As is apparent from the foregoing detailed disclosure, this embodiment of the present invention functions in substantially the same manner as the first embodiment, providing effective and complete mixing of the bone cement in a completely sealed chamber until the entire bone cement has been completely formed. Once the cement is completely intermixed, the user is able to automatically advance the mixed cement through the delivery tube directly to the desired site. In addition, all of the features detailed above relating to the automatic delivery of the bone cement to outlet portal 61 is equally applicable, as well as the construction of movement controlling portion 30 so as to eliminate any entrapped air from the cement and provide the desired delivery pressure level. Consequently, this embodiment, like the previous embodiment, attains substantially air-free mixed bone cement delivered to the precisely desired site under pressure. In addition, if the use of a vacuum source is desired, to further assure the removal of any entrapped air, cover 24 may be constructed with a vacuum, as detailed above.

In the same manner detailed above, the distal end of delivery tube 23 incorporates thread means 67 so as to accommodate an extension tube, if needed. In this way, the mixed cement bone cement can be delivered directly to any desired location or position with the required pressure to provide the desired bone cement bonding.

In FIGS. 12–16, a further embodiment for constructing a fully integrated bone cement mixing and delivering system 20 in accordance with the present invention is fully detailed. As with the embodiments detailed above, similar reference numerals are employed throughout the following disclosure and associated drawings for referring to similar structural elements. Consequently, all of the detailed disclosure provided above regarding these components is intended to have equal efficacy and effect on the structure shown in FIGS. 12–16. Furthermore, in order to avoid repetition of unnecessary disclosure, many of the details of the similar structural arrangements are not provided hereafter, due to the full disclosure in the foregoing discussion regarding these components and the constructions thereof.

In the embodiment detailed in FIGS. 12–16, mixing/delivery system 20 comprises housing 21 which incorporates a mixing chamber 22 and delivery tube 23, integrally interconnected and cooperatively associated with mixing chamber 22. In addition, integrated mixing/delivery system 20 also comprises a removable cover 101 which is mountable to mixing chamber 22.

In this embodiment, cover 101 is constructed with thread means 102 formed in the interior surface thereof, while mixing chamber 22 comprises cooperating thread means 103 formed on outer wall 45 of mixing chamber 22. In addition, circular shaped recess 104 is formed in cover 101 preferably positioned above thread means 102 with O-ring 105 constructed for being mountingly retained in recess 104.

In this way, when cover 101 is threadedly mounted to mixing chamber 102, by employing threads means 102 and 103, the secure, sealed, mounted engagement of cover 101 with mixing chamber 22 is assured. Furthermore, all unwanted seepage of the bone cement mixture from the interior of mixing chamber 22 through cover 101 is completely avoided, due to the threaded sealing interengagement between cover 101 and chamber 22 as well as by the sealing mounted engagement of O-ring 105 in peripheral surrounding, sealing contact with outside wall 45 of chamber 22.

As detailed above in the discussion regarding the previous two embodiments, this embodiment of mixing/delivery system 20 also incorporates elongated, multi-component shaft member 28 comprising mixing portion 29 and movement controlling portion 30. In this embodiment, a construction substantially equivalent to the construction detailed above is employed. Consequently, the complete, extensive disclosure provided above regarding the preferred construction, as well as the alternate construction for multi-component shaft member 28, as well as mixing portion 29 and movement controlling portion 30, is equally applicable to this embodiment of the present invention. Furthermore, a uniform diameter rod member may be employed as part of movement controlling portion 30 or, if desired, a tapered diameter construction, as shown in FIG. 6 and fully discussed above. Regardless of which embodiment is employed, equal efficacy and performance results are obtained using this third embodiment of the present invention.

In order to enable elongated, multi-component shaft member 28 to be rotationally driven, as provided in the previous embodiments, cover 101 incorporates a centrally disposed aperture 106 constructed for cooperating relationship with rod member 34 of mixing portion 29. By employing this construction, as previously detailed, terminating end 38 of rod member 34 is easily, controllably interengaged with suitable drive means for providing the operator controlled rotation of elongated, multi-component shaft member 28.

In this embodiment, both mixing portion 29 and movement controlling portion 30 are preferably constructed in a manner substantially identical to the construction detailed above. In this regard, at least two mixing blades 35,35 radially extend from elongated rod member 34 and are formed in an arcuately curved shape, with the outer edge 56 of each mixing blade 35 having a size and shape constructed for cooperative interrelationship with inside wall 46 of mixing chamber 22. In addition, movement controlling portion 30 comprises continuous, ramped, radially extending helical-shaped auger or screw thread member 63 extending from rod member 64. As depicted in FIGS. 12–14, rod member 64 comprises a substantially uniform diameter.

However, as briefly mentioned above, rod member 69, with a tapered diameter as depicted in FIG. 6 and fully discussed above, can be employed with equal efficacy and effect as well as the other rod member embodiments discussed above.

The principal distinguishing features of the embodiment depicted in FIGS. 12–16 and the embodiments detailed above and shown in FIGS. 1–11 is found in construction and cooperative interengagement between mixing chamber 22 and delivery tube 23. In this embodiment, a still further unique construction is employed for establishing cooperating interengagement between mixing chamber 22 and delivery tube 23, as well as establishing and effectively providing a first sealed position, wherein the interior of mixing chamber 22 is completely sealed from the interior of delivery chamber 23, and a second position, wherein the interior zones of mixing chamber 22 and delivery tube 23 are in cooperating communication with each other.

In this embodiment, mixing chamber 22 comprises a substantially U-shape, formed by outer wall 45 and inner wall 46. In addition, mixing chamber 22 comprises an enlarged, open entry zone 47 formed at the top of substantially U-shaped chamber 22 which is constructed for cooperative, sealed interengagement with cover 101 and O-ring 105 as detailed herein.

Furthermore, in the construction of mixing chamber 22 of this embodiment, the base or lower portion of mixing chamber 22 comprises a substantially circular shaped opening or passageway 80 which extends from the interior of mixing chamber 22 outwardly therefrom. At the terminating end of passageway 80, two juxtaposed, spaced, cooperating wall members 110 and 111 are positioned extending from surface 117, adjacent the outlet of passageway 80 to bottom 82 of mixing chamber 22. Since wall members 110 and 111 are independent from each other, and are formed in juxtaposed, spaced, cooperating relationship, an elongated open zone 112 is formed therebetween, directly communicating with passageway 80.

The construction of mixing chamber 22 is completed by incorporating a plurality of screw receiving holes in bottom surface 82 thereof. As detailed below, screw receiving holes are positioned for cooperating relationship with a portion of delivery tube 23 and screw means associated therewith.

In this embodiment, delivery tube 23 is formed as separate and independent cooperating components. As depicted in FIGS. 12–14, delivery tube 23 comprises axially movable, cylindrical tube portion 120 and fixedly mounted base portion 121. In the preferred construction of this embodiment, tube portion 120 comprises an elongated, substantially cylindrical shape formed by outer wall 123 and inner wall 124. Recesses or grooves 125, 126, and 127 are formed in outer wall 123 at various spaced locations along outer wall 123. Preferably, recess 125 is formed near the proximal end of tube portion 120, while recess 127 is formed near the distal end thereof. Furthermore, a pair of arm members 128 and 129 are formed on tube portion 120, radially extending outwardly from outer wall 123, positioned adjacent the distal end of tube portion 120.

As shown in FIGS. 12–14, the diameter of outer wall 123 of tube portion 120 is constructed for cooperating, sliding interengagement with passageway 80 of mixing chamber 22. As a result, the diameter of outer wall 123 of tube portion 120 is substantially equivalent to or slightly less than the diameter of passageway 80. In this way, tube portion 120 is axially movable relative to passageway 80 of mixing chamber 22 when desired, with arm members 128 and 129 being positioned between walls 110 and 111.

In addition to providing cooperating dimensions between tube portion 120 and mixing chamber 22 which substantially eliminates any unwanted seepage of the bone cement during the mixing operation between passageway 80 and outer wall 123 of tube portion 120, O-rings 130 are mounted in recesses 125, 126, and 127. By incorporating a separate O-ring 130 in each of the recesses formed in outer wall 123 of tube portion 120, the area between outer wall 123 and passageway 80 of mixing vessel 22 is effectively sealed, while still assuring that the desired axial sliding movement of tube portion 120 relative to mixing vessel 22 is easily attained.

Completing the construction of delivery tube 23 for this embodiment of the present invention, base portion 121 comprises a support plate 134 on which two juxtaposed, spaced, upstanding posts 135 and 136 extend in one direction while a substantially cylindrically shaped conduit 137 extends in the opposed direction.

Plate 134 incorporates a plurality of through holes formed therein peripherally surrounding conduit 137 and positioned for cooperative alignment with screw receiving holes of mixing vessel 22. By employing screw means 138, base portion 121 is securely affixed to bottom 82 of mixing vessel 22.

Base portion 121 of delivery tube 23 incorporates outlet portal 61 at the distal end of conduit 137. In addition, conduit 137 also incorporates ledge 70 for receiving and maintaining distal end 66 of movement controlling portion 30 in the desired position, aligned with outlet portal 61 for assuring the secure, continuous rotation of movement controlling portion 30 and the delivery of the mixed bone cement through outlet portal 61 to the desired location under pressure.

In this embodiment, post 135 and 136 of base portion 121 are constructed for being positioned between wall members 110 and 111 in cooperating relationship therewith. Furthermore, post 135 and 136 extend substantially perpendicularly from plate 134 a sufficient distance to provide a space between the ends of posts 135 and 136 and surface 117 from which walls 110 and 111 extend. Preferably, this spacing is at least equal to the thickness of radially extending arms 128 and 129 of tube portion 120, in order to enable arms 128 and 129 to be retained within the space, while also being removable therefrom, whenever desired. By employing this construction, radially extending arms 128 and 129 are independently retained on either post 135 or 136, preventing axial movement of tube portion 120 relative to mixing vessel 22. However, whenever desired by the user, arms 128 and 129 are pivotable to be withdrawn from retained engagement with posts 135 and 136, thereby releasing tube portion 120 from its axially immovable position into a position which enables the axial movement of tube portion 120 relative to mixing vessel 22.

In the preferred construction of this embodiment of the present invention, an automatically engaged lock system is provided to retain mixing/delivery system 20 in the second position, once the second position has been attained by the user. As best seen in FIGS. 15–17, this automatic lock system is attained by providing wall members 110 and 111 with an elongated rib 140 extending from the surface thereof, positioned in juxtaposed, spaced relationship with post 135 or 136. In the preferred construction, rib 140 extends substantially the entire length of the edge surface of wall members 110 and 111 on which it is mounted, while terminating at a spaced distance from plate 134 of base portion 121. The spaced distance remaining between the surface of plate 134 and the terminating edge of rib 140 is substantially equivalent or slightly greater than the thickness of arm members 128 and 129.

In addition, posts 135 and 136 each comprise a side surface 141, which is constructed with a continuous slope, providing a greater spaced distance from rib 140 near the terminating end of posts 135 and 136, while being substantially closer to rib 140 as surface 141 contacts plate 134. In the preferred construction, the spaced distance of sloping surface 141 from the side edge of wall 110 and 111 at the juncture with plate 134 represents a distance substantially equivalent to the width of arm members 128 and 129.

The lock construction is completed by incorporating in each arm member 128 and 129 a flexible finger portion 141 formed along the side edge of arm members 128 and 129 facing rib 140. By employing this construction, whenever axially movable, cylindrical tube portion 120 of tube member 123 is to be moved from its first position into its second, cement delivering position, arm members 128 and 129 are arcuately pivoted about the central axis of tube portion 120 in order to cause arm members 128 and 129 to be removed from captured engagement between the top surface of posts 135 and 136 and support surface 117 of mixing chamber 22. Once arm members 128 and 129 are removed from the captured position and arcuately pivoted into open zone 112, arm members 128 and 129 are free to be axially moved towards plate 134, simultaneously causing cylindrical tube portion 120 to be controllably moved therewith.

As arm members 128 and 129 are advanced towards plate 134, side edge 143 of arm members 128 and 129 contact sloping surface 141 of posts 135 and 136, causing arm members 128 and 129 to advance towards wall members 110 and 111 and rib 140 extending therefrom. As arm members 128 and 129 are continuously advance towards plate 134, causing cylindrical tube portion 120 to be axially moved therewith, flexible finger 142 of arm members 128 and 129 are brought into contact with rib 140, causing flexible finger 142 of each arm member 128 and 129 to be flexed inwardly towards arm member 128 and 129. This flexing or deflection of finger 142 continues until arm members 128 and 129 have been advanced into contact with plate 134 of base portion 121.

Once in this position, flexible fingers 142 of arm members 128 and 129 are disengaged from contacting relationship with rib 140, due to its spaced distance away from plate 134, thereby enabling flexible fingers 142 to return to their original position. Once in this position, flexible fingers 142 of arm members 128 and 129 are in locked interengagement with ribs 140, thereby preventing cylindrical tube portion 120 to be returned from the second position to the first position. In this way, the secure, automatic, locked engagement of cylindrical tube portion 120 in the second position is provided.

As best seen in FIGS. 13 and 14, when this embodiment of mixing/delivery system 20 is fully assembled and placed in its first, closed position, with the interior of mixing chamber 22 completely independent from the interior of delivery tube 23, radially extending arms 128 and 129 are captured and maintained in position locked between the terminating ends of posts 135 and 136 and support surface 117 of mixing vessel 22. When mixing/delivery system 20 is in this position, the upper proximal end of cylindrical tube portion 120 of delivery tube 23 is maintained within aperture 80 of mixing vessel 22, while also extending into the bottom of mixing chamber 22 in peripheral, surrounding and sealing relationship with ramped, radially extending, helical shaped auger or screw thread member 63 of movement controlling portion 30. As a result, any contact of screw thread member 63 with the bone cement is prevented and all the bone cement is safely maintained within the interior of mixing chamber 22.

In order to assure secure, seepage-free separation of the bone cement from movement controlling portion 30, the proximal end of cylindrical tube portion 120 with O-ring 130 within recess 125 is inserted within grooves 118 formed at the distal end of rod member 34 of mixing portion 29. In this way, complete sealing of movement controlling portion 30 from exposure to the bone cement within the interior of mixing chamber is attained, when mixing delivery chamber 20 is in its first position.

In order to move mixing/delivery system 20 from its first position into its second position, wherein the interior of mixing chamber 22 is in communication with the interior of cylindrical tube portion 120 of delivery tube 23, cylindrical tube portion 120 is arcuately rotated about its central axis by controllably moving radially extending arms 128 and 129 out of retained engagement with posts 135 and 136, as discussed above. Once arms 128 and 129 are positioned within open zone 112, cylindrical tube portion 120 of delivery tube 23 is capable of axial, telescopic movement, in its entirety, relative to mixing vessel 22.

When cylindrical tube portion 120 of delivery tube 23 is axially moved towards base portion 121, by advancing arm members 128 and 129 toward base portion 121, the proximal end of cylindrical tube portion 120 is moved away from sealing engagement with groove 118 of rod member 34 of mixing portion 29. In this way, the proximal end of movement controlling portion 30 is exposed to the interior of mixing chamber 22.

When the axial movement of tube portion 120 is completed, as depicted in FIG. 14, continuous, ramped, radially extending helical-shaped auger/screw thread member 63 is fully exposed to the bone cement contained within mixing chamber 22. As a result, when elongated, multi-component shaft member 28 is rotated, the mixed cement is effectively advanced from chamber 22 through cylindrical tube portion 120 of delivery tube 23 until the desired mixed bone cement has been transferred through tube portion 120, conduit 137 of base portion 121 and through outlet portal 61.

As is apparent from the foregoing detailed disclosure, this embodiment of the present invention operates in substantially the same manner as the first two embodiments, providing effective and complete mixing of the bone cement in a completely sealed chamber until the entire bone cement has been completely formed. Once the cement is completely intermixed, the user is able to automatically advance the mixed bone cement through the delivery tube directly to the desired site. In addition, all of the features detailed above relating to the automatic delivery of the bone cement to outlet portal 61 is equally applicable, as well as the construction of movement controlling portion 30, so as to eliminate any entrapped air from the cement and provide the desired pressure at the bone being treated. Consequently, this embodiment, like the previous embodiments, attains substantially air-free mixed bone cement delivered to the precisely desired site under pressure in a fully integrated system, without requiring exposure of the noxious odor or the bone cement to the user. Furthermore, if desired, the system may be connected to a vacuum source for further removal of entrapped air.

In the same manner detailed above, the end of conduit 137 of base portion 121 of delivery tube 23 incorporates thread means 67, so as to accommodate an extension tube if needed. In this way, the mixed bone cement is able to be delivered directly to any location or position desired by the user.

If desired, the embodiment depicted in FIGS. 7–11 may also be constructed to provide secure locked engagement of radially extending arms 90 and 91 when the arms are moved from the first position to the second position. In order to establish this interlocked position, a construction similar to the construction detailed above in reference to FIGS. 12–17 may be employed. In this regard, by referring to FIGS. 10, 11, and 18, the implementation of a lock system with this embodiment can best be understood.

Preferably, the automatic lock system is attained by providing an elongated ramp 100 formed on the inside walls of zone 81 positioned for cooperation with radially extending arms 90 and 91. Preferably, each elongated rib 100 extends from a wall of mixing vessel 22 in juxtaposed, spaced relationship with upstanding posts 95 terminating at a spaced distance from plate 93. The spaced distance remaining between the surface of plate 93 and the terminating edge of rib 100 is substantially equivalent or slightly greater than the thickness of arm members 90 and 91.

In addition, upstanding posts 95 each comprise a side surface 108 which is constructed with a continuous slope, providing a greater spaced distance from rib 100 near the terminating end of posts 95, while being substantially closer to rib 100 as surface 108 contacts plate 93. In the preferred construction, the spaced distance of sloping surface 108 from the wall defining open zone 81 at the juncture with plate 93 represents a distance substantially equivalent to the overall width of arm members 90 and 91.

The lock construction is completed by forming each arm member 90 and 91 with a flexible finger 109 formed along the side edge of arm members 90 and 91 facing rib 100. By employing this construction, whenever axially movable, cylindrical delivery tube 23 is moved from its first position into its second position, arm members 90 and 91 are arcuately pivoted about the central axis of delivery tube 23 causing the arm members 90 and 91 to be removed from engagement on posts 95 into open zone 81. Once arm members 90 and 91 are moved into open zone 81, arm members 90 and 91 are free to be axially moved towards plate 93, simultaneously causing delivery tube 23 to be controllably moved therewith.

As arm members 90 and 91 are advanced towards plate 93, the side edge of each arm member contacts sloping edge 108 of posts 95, causing arm members 90 and 91 to advance towards rib 100. As arm members 90 and 91 are continuously advanced towards plate 93, causing delivery tube 23 to be axially moved therewith, flexible fingers 109 of arm members 90 and 91 are brought into contact with rib 100, causing fingers 109 of each arm member 90 and 91 to be flexed inwardly towards the arm member. This flexing or deflection of finger 109 continues until arm members 90 and 91 have been advanced into contact with plate 93. Once in this position, flexible fingers 109 of arm members 90 and 91 are disengaged from contacting relationship with rib 100, due to its spaced distance away from plate 93, thereby enabling flexible fingers 109 to return to their original position. Once in this position, flexible fingers 109 of arm members 90 and 91 are in locked interengagement with rib 100, thereby preventing delivery tube 23 from being returned from its second position to its first position. In this way, the secure, automatic, locked engagement of delivery tube 23 in its second position is provided.

As discussed above, as well as depicted throughout the drawings, mixing blades 35,35 are mounted to rod member 34 with an outer edge 54 which is arcuately curved relative to the central axis of rod member 34. In the embodiment discussed and depicted above, each outer edge 54 of each mixing blade 35 comprises an arcuate radius of about 90°. In general, it has been found that a construction of this nature provides superior results while also assuring that the bone cement components are controllably advanced towards the rotating movement controlling portion 30 regardless of the particular orientation of mixing/delivery system 20.

Although an arcuate radius of 90° for outer edge 54 of mixing blade 35 has been found to be particularly efficacious, alternate arcuate radii may also be employed without departing from the scope of this invention. In fact, as discussed above, the arcuate radius may range between 45° and 360° in achieving mixing blades capable of functioning in the present invention.

Figure 21:
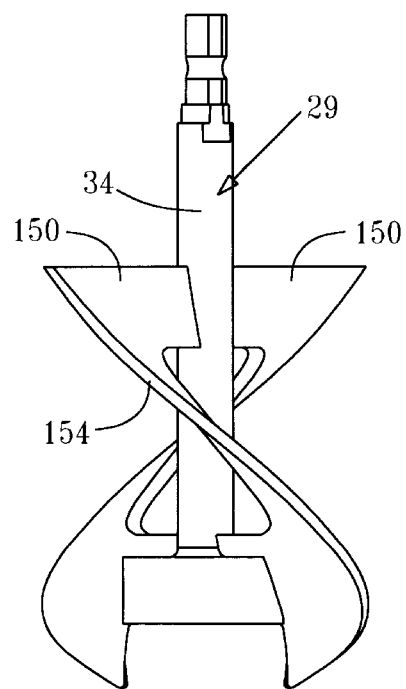
FIG. 21 is a side elevation view detailing an alternate embodiment of the mixing portion forming a component of the integrated mixing and delivery system of the present invention.
Figure 22:
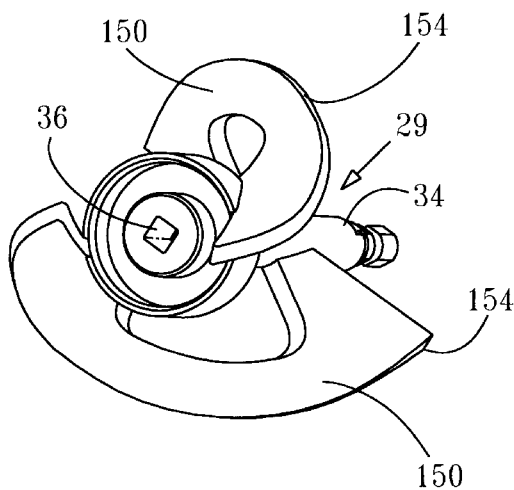
FIG. 22 is a bottom perspective view of the mixing portion of FIG. 21.

In FIGS. 21 and 22, an alternate embodiment to the mixing blade construction depicted in the foregoing figures is provided. In this embodiment, mixing portion 29 comprises an elongated rod member 34 having two mixing blades 150,150 extending therefrom with the terminating edge 154 of each mixing blade 150,150 comprising an arcuate radius substantially equal to 165° degrees.

By employing this embodiment, it has been found that the components forming the bone cement are thoroughly intermixed and controllably advanced towards movement controlling portion 30, when desired, virtually independently of the position in which mixing/delivery system 20 is placed. As a result, by employing mixing blades 150,150 with an outer edge 154 having an arcuate radius of about 165°, a mixing/delivery system 20 is attained which is capable of thoroughly intermixing the components forming the bone cement as well as advancing the bone cement from the mixing zone to the delivery zone regardless of the position or orientation in which mixing/delivery system 20 is placed. As a result, substantially enhanced flexibility, adaptability and control is attained by mixing/delivery system 20 of the present invention.

As briefly mentioned above, mixing/delivery system 20 of the present invention may incorporate indicator means 160 in order to provide the user with a positive indication when the components of the bone cement are thoroughly intermixed. Although various alternate embodiments for indicator means can be employed, the preferred construction of the present invention is depicted in FIGS. 23 and 24.

As shown in this embodiment, indicator means 160 comprises a plurality of cooperating gear members 162 which are constructed to measure the number of times rod member 34 of mixing portion 29 has been rotated. In tests conducted on the mixing of bone cement, it has been found that neither the rotational speed nor time are the controlling factors in determining when the components of the bone cement have been thoroughly intermixed. Instead, the number of actual revolutions the mixing blades make through the components has been found to provide the best measure of determining when the bone cement has been fully intermixed. As a result, indicator means 160 is constructed to provide this desired measurement.

Figure 23:
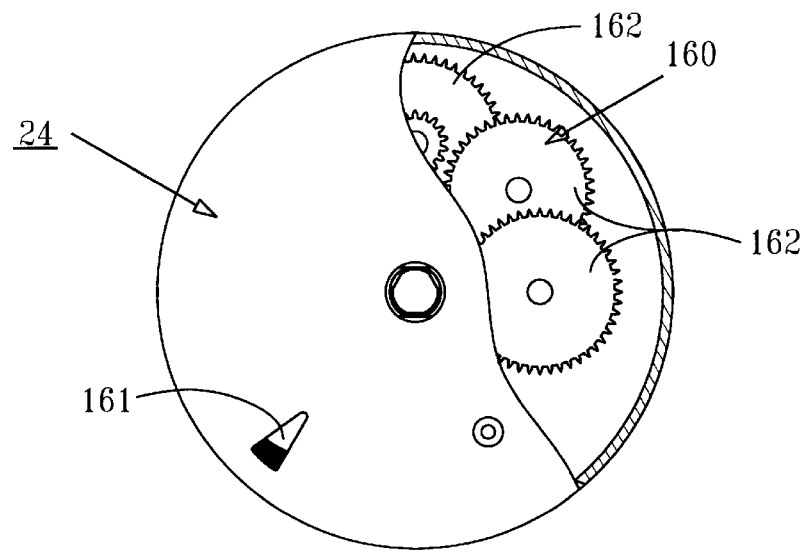
FIG. 23 is a top plan view, partially broken away, depicting the construction of indicator means formed in the cover of the integrated mixing and delivery system of the present invention.
Figure 24:
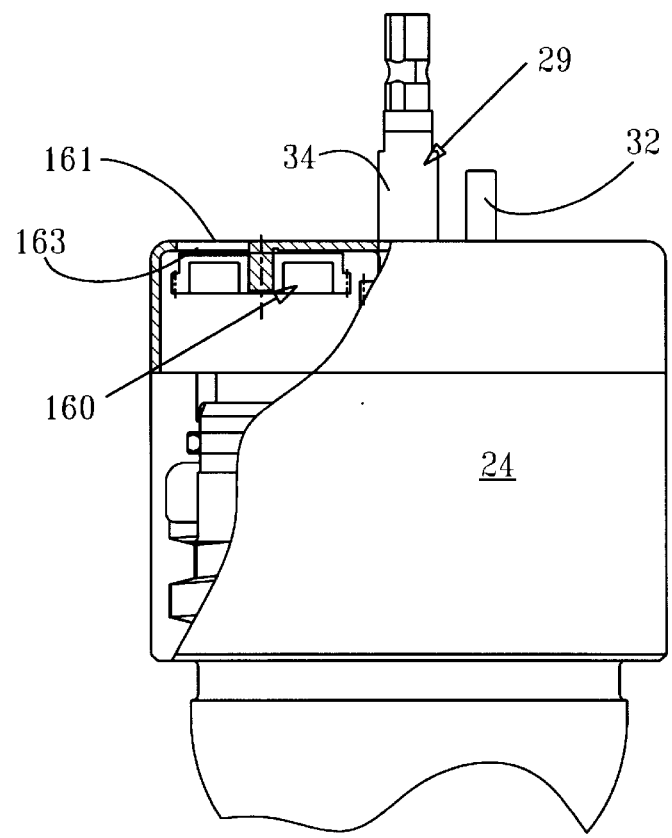
FIG. 24 is a side elevation view, partially in cross-section and partially broken away, providing further depiction of the indicator means of FIG. 23.

In the preferred embodiment depicted in FIGS. 23 and 24, indicator means 160 comprises a plurality of gear members 162 which are driven by the rotation of rod member 34 of mixing portion 29. In addition, indicator means 160 comprises a highly visible status indicator plate 163 which is mounted in cooperating association with window 161 formed in cover 24 in order to enable indicator plate 163 to be easily viewed throughout the mixing operation.

In the preferred construction, indicator plate 163 provides a plurality of status markings printed thereon which represents the various stages experienced by this bone cement during the mixing operation. By employing appropriate indicia, such as color, the precise status of the bone cement is represented through window 161.

In order to provide a positive, accurate indication of the progress of the mixing operation of the bone cement, indicator plate 163 is constructed for movement relative to window 161. In addition, gear members 162 of indicator means 160 are constructed to provide the positive movement for indicator plate 163 relative to window 161 in direct association with the number of rotations rod member 34 of mixing portion 29 has experienced. Consequently, by constructing indicator means 160 with the proper gear ratio for driving indicator plate 163 in the proper manner, indicator plate 163 provides the user with a precise visual measurement of the mixing process as well as a positive indication when rod member 64 has been rotated a sufficient number of revolutions to assure the bone cement is completely intermixed. As a result, by employing this construction, ease of operation is further enhanced with the user being provided a virtually a full-proof construction wherein mere visual observation of an indicator immediately informs the user when the bone cement is ready for use.

It will thus be seen that the objects set forth above, among those made apparent from the preceding description, are efficiently attained and, since certain changes may be made in the above construction, without departing from the scope of the invention, it is intended that all matter contained in the above description or shown in the accompanying drawings shall be interpreted as illustrative and note in a limiting sense.

It is also to be understood that the following claims are intended to cover all of the generic and specific features of the invention herein described, and all statements of the scope of the invention, which as a matter of language, might be said to fall therebetween.

Having described our invention, what we claim as new and desire to secure by Letters Patent is:

1. An integrated mixing and delivering system for fully intermixing bone cement components and delivering the mixed bone cement to a desired location, said system comprising:

A. a mixing vessel having
        a. an enlarged entry portal for receiving the bone cement components, and
        b. an exit portal positioned for enabling the mixed bone cement to pass therethrough;
    B. cover means removably mountable to the mixing vessel in covering engagement with the entry portal;
    C. an elongated delivery tube comprising
        a. a proximal end mounted to the exit portal of the mixing vessel in cooperating association therewith,
        b. a distal end incorporating a cement delivering outlet portal, and
        c. an elongated interior delivery zone extending between the proximal end and the outlet portal;
    D. at least one mixing blade removably mountable in the mixing vessel and being rotationally driven therein for fully intermixing the components forming the bone cement;
    E. elongation movement control means
        a. removably mounted in axially extending relationship in the delivery tube extending substantially the entire length thereof, b. rotationally movable within the delivery tube, and c. constructed for receiving the mixed bone cement at the proximal end of the delivery tube and controllably advancing the mixed cement through the delivery tube to the outlet portal due to the rotating movement thereof; and F. position control means cooperatively associated with the delivery tube and the mixing vessel to enable the delivery tube to be movable from
   a. a first position wherein the interior of the mixing vessel and the interior delivery zone of the delivery tube are sealed from each other, and
   b. a second position wherein the interior of the mixing vessel and the interior zone of the delivery tube are in communication with each other;

whereby the bone cement components are fully intermixed in a separate zone completely sealed from the delivery tube and, once the cement is mixed, the mixing vessel and delivery tube are moved into communication with each other, enabling the mixed cement to be controllably advanced from the mixing vessel to the outlet portal for direct use.

2. The integrated mixing and delivery system defined in claim 1, wherein said mixing vessel comprises a substantially U-shaped interior mixing zone with the exit portal formed at the base thereof.

3. The integrated mixing and delivery system defined in claim 2, wherein said delivery tube is further defined as comprising an elongated, hollow, substantially cylindrical shape with the proximal end thereof constructed for cooperative inserted interengagement with the exit portal of said mixing vessel.

4. The integrated mixing and delivery system defined in claim 1, wherein said position control means is further defined as comprising:
   c. a support plate mountable to the mixing vessel and incorporating a pair of upstanding post members extending therefrom, and
   d. a pair of radially extending arm means formed on the delivery tube and positioned for cooperative arcuate movement between the post members enabling the delivery tube to be movable from a first position, peripherally surrounding and sealing the movement control means from the interior of the mixing vessel to a second position, wherein the proximal end of the delivery tube is axially moved away from said exit portal of the mixing vessel, thereby enabling the mixed bone cement to easily contact and be controllably moved by the movement control means.

5. The integrated mixing and delivery system defined in claim 4, wherein each of said upstanding post members is further defined as comprising a ramped surface positioned in juxtaposed spaced facing relationship with an elongated locking rib formed on a facing adjacent wall and said radially extending arm members are further defined as comprising a flexible finger portion constructed for cooperative sliding contact along the locking rib, flexing in a first direction as the radially extending arm means is advanced from the first position to the second position, and returning to its original position in locked interengagement with the rib when said arm means is in its second position.

6. The integrated mixing and delivery system defined in claim 1, wherein said delivery tube is further defined as comprising a fixedly mounted base portion incorporating the outlet portal and an axially movable, cylindrically shaped tube portion positioned between the base portion and the mixing vessel, controllably movable from a first position wherein the proximal end thereof is within the mixing vessel peripherally surrounding and sealing the movement control means therefrom and a second position, wherein said proximal end is axially moved away from engagement with the exit portal of the mixing vessel, thereby enabling the mixed bone cement to be in contact with the movement control means.

7. The integrated mixing and delivery system defined in claim 1, wherein said mixing blade is further defined as being affixed to an elongated rod member for rotationally driving the mixing blades within the mixing vessel and said cover means is further defined as comprising a centrally disposed aperture constructed for cooperating, peripheral surrounding engagement with the rod member enabling the mixing blades and the rod member to be easily rotated externally of the mixing vessel.

8. The integrated mixing and delivery system defined in claim 7, wherein said rod member is constructed for being rotationally driven externally of the mixing vessel by engagement with one selected from the group consisting of electronically driven rotational drivers and hand cranks.

9. The integrated mixing and delivery system defined in claim 7, wherein said cover is further defined as comprising seal means for assuring secure sealing interengagement of said cover with said mixing vessel.

10. The integrated mixing and delivery system defined in claim 1, wherein said system further comprises:
   G. indicator means mounted to the mixing vessel for measuring the progress of the mixing of the bone cement and providing a positive indication to the user when the bone cement has been fully intermixed.

11. The integrated mixing and delivery system defined in claim 10, wherein said indicator means is further defined as comprising gear means constructed for measuring the rotational revolutions of the mixing blades and providing a positive indication to the user once sufficient rotation of the mixing blades has been achieved to assure a fully intermixed bone cement product.

12. An integrated mixing and delivery system for fully intermixing bone cement components and delivering the mixed bone cement to a desired location, said system comprising:
   A. a mixing vessel having
      a. an enlarged entry portal for receiving the bone cement components, and
      b. an exit portal positioned for enabling the mixed bone cement to pass therethrough:
   B. cover means removably mountable to the mixing vessel in covering engagement with the entry portal;
   C. an elongated delivery tube comprising an elongated hollow member incorporating
      a. a proximal end mounted to the exit portal of the mixing vessel in cooperating association therewith,
      b. a distal end incorporating a cement delivering outlet portal, and
      c. an elongated interior delivery zone extending between the proximal end and the outlet portal;
   D. at least one said mixing blade affixed to a first elongated rod member and removably mountable in the mixing vessel and being rotationally driven therein for fully intermixing the components forming the bone cement;
   E. movement control means comprising substantially continuous, ramped, radially extending, helical or spiral shaped threads formed on a second elongated rod member and being removably mountable in the delivery tube and constructed for receiving the mixed bone cement at the proximal end of the delivery tube and controllably advancing the mixed cement through the delivery tube to the outlet portal; and F. position control means cooperatively associated with the delivery tube and the mixing vessel to enable the delivery tube to be movable from
   a. a first position wherein the interior of the mixing vessel and the interior delivery zone of the delivery tube are sealed from each other, and
   b. a second position wherein the interior of the mixing vessel and the interior zone of the delivery tube are in communication with each other;

whereby the bone cement components are fully intermixed in a separate zone completely sealed from the delivery tube and, once the cement is mixed, the mixing vessel and delivery tube are moved into communication with each other, enabling the mixed cement to be controllably advanced from the mixing vessel to the outlet portal for direct use.

13. The integrated mixing and delivery system defined in claim 12, wherein said first rod member and said second rod member are constructed for cooperative interengagement and simultaneous rotation about the central axis thereof.

14. The integrated mixing and delivery system defined in claim 13, wherein said first rod member and second rod member are further defined as being removably interconnectable to each other for enabling said first rod member and second rod member to cooperatively function as a substantially single, integrated, elongated component.

15. The integrated mixing and delivery system defined in claim 13, wherein said cover means is further defined as comprising a substantially centrally disposed aperture formed therein constructed for enabling the first rod member to extend therethrough for being rotationally driven by external rotation inducing drive means.

16. The integrated, mixing and delivery system defined in claim 15, wherein said second rod member is further defined as comprising an overall tapered configuration, having a smaller diameter at the end thereof interconnected to the first rod member and a larger diameter at the opposed end thereof.

17. The integrated mixing and delivery system defined in claim 16, wherein said tapered rod member is further defined as comprising a diameter ranging between about 0.18 inches and 0.50 inches throughout the length thereof.

18. The integrated mixing and delivery system defined in claim 12, wherein said second rod member is further defined as comprising a substantially uniform diameter throughout its length.

19. The integrated mixing and delivery system defined in claim 12, wherein said second rod member is further defined as comprising a uniform diameter throughout its length.

20. The integrated mixing and delivery system defined in claim 12, wherein said second rod member is further defined as comprising a funnel shape having a larger diameter adjacent the mixing vessel and a smaller diameter at the distal end thereof.

21. The integrated mixing and delivery system defined in claim 12, wherein said radially extending, ramped, helical or spiral shaped thread members are further defined as comprising a pitch throughout the length of said second rod member selected from the group consisting of variable pitches and uniform pitches.

22. The unitary mixing and delivery system defined in claim 21, wherein said radially extending, continuous, ramped, helical or spiral thread member is further defined as comprising a variable pitch with said pitch being formed by the spacing between adjacent thread members, said spacing ranging between about 1.25 and 0.10 inches.

23. The integrated mixing and delivery system defined in claim 22, wherein said spacing is further defined as being larger at the proximal end of said second rod member and comprising a smaller distance at the distal end of said second rod member.

24. The integrated mixing and delivery system defined in claim 12, comprising at least two mixing blades, each of which are arcuately curved relative to the first rod member with the outer edge thereof conforming to the inside wall of said U-shaped mixing zone.

25. The integrated mixing and delivery system defined in claim 24, wherein each of said arcuately curved mixing blades is further defined as comprising an outer edge defining an arc ranging between about 45° and 360°.

26. The integrated mixing and delivery system defined in claim 25, wherein said curved outer edge of each mixing blade is further defined as comprising an arc ranging between about 90° and 180°.

27. The integrated mixing and delivery system defined in claim 12, wherein said cover means is further defined as being sealable about the entry portal of the mixing vessel, thereby preventing any unwanted seepage of bone cement during the mixing process.

28. The integrated mixing and delivery system defined in claim 12, wherein said system is further defined as comprising a vacuum port cooperatively associated with the mixing vessel to enable the mixing vessel to be exposed to a vacuum source during the mixing and delivery process.

29. The integrated mixing and delivery system defined in claim 28, wherein said vacuum port is affixed to the cover means in order to provide a readily accessible interconnection for said vacuum source.

30. The integrated mixing and delivery system defined in claim 12, wherein said mixing vessel comprises a substantially U-shaped interior mixing zone and the exit portal is formed at the base thereof, and said elongated, hollow delivery tube is further defined as comprising a substantially cylindrical shape.

31. An integrated mixing and delivery system for fully intermixing bone cement components and delivering the mixed bone cement to a desired location, said system comprising:

A. a mixing vessel having
   a. an enlarged entry portal for receiving the bone cement components, and
   b. an exit portal positioned for enabling the mixed bone cement to pass therethrough;

B. cover means removably mountable to the mixing vessel in covering engagement with the entry portal;

C. an elongated hollow delivery tube comprising
   a. a proximal end in cooperative interengagement therewith,
   b. a distal end incorporating a cement delivery outlet portal, and
   c. an elongated interior delivery zone extending between the proximal end and the outlet portal;

D. at least one mixing blade affixed to a first elongated rod member and removably mountable in the mixing vessel for being rotationally driven therein for fully intermixing the components forming the bone cement;

E. movement control means removably mounted in the delivery tube and constructed for receiving the mixed bone cement at the proximal end of the delivery tube and controllably advancing the mixed cement through the delivery tube to the outlet portal; and F. position control means
   a. cooperatively associated with the delivery tube and the mixing vessel to enable the delivery tube to be movable from
      1. a first position wherein the interior of the mixing vessel and the interior delivery zone of the delivery tube are sealed from each other, and
      2. a second position wherein the interior of the mixing vessel and the interior zone of the delivery tube are in communication with each other, and
   b. comprising a support plate radially extending from the delivery tube and holding means mountable to the mixing vessel with the support plate of the delivery tube positioned therebetween to enable the arcuate movement of the delivery tube relative to the mixing vessel, with portal zones formed in the proximal end of said delivery tube, cooperating with the exit portal of the mixing vessel, said position control means providing a first position wherein said portals are sealed from each other and a second position wherein said portals are aligned, enabling communication therebetween;

whereby the bone cement components are fully intermixed in a separate zone completely sealed from the delivery tube and, once the cement is mixed, the mixing vessel and delivery tube are moved into communication with each other, enabling the mixed cement to be controllably advanced from the mixing vessel to the outlet portal for direct use.

32. The integrated mixing and delivery system defined in claim 31, wherein said position control means further comprises a cam surface formed on the support plate radially extending from the delivery tube and a cam follower formed on the mixing vessel cooperatively associated with the cam surface to define the arcuate movement of the delivery tube relative to the mixing vessel, thereby establishing the two alternate positions thereof.

33. An integrated mixing and delivering system for fully intermixing bone cement components and delivering the mixed bone cement to a desired location, said system comprising:

A. a mixing vessel having
   a. an enlarged entry portal for receiving the bone cement components, and
   b. an exit portal positioned for enabling the mixed bone cement to pass therethrough;

B. cover means removably mountable to the mixing vessel in covering engagement with the entry portal;

C. an elongated hollow delivery tube comprising
   a. a proximal end constructed for telescopic sliding engagement with the exit portal of the mixing vessel,
   b. a distal end incorporating a cement delivering outlet portal,
   c. an elongated interior delivery zone extending between the proximal end and the outlet portal, and
   d. a structure for peripherally surrounding and blocking movement control means when said delivery tube is in a first position, while revealing a portion of the movement control means when said delivery tube is moved to a second position, thereby assuring exposure of the movement control means to the mixed bone cement in the mixing vessel when desired;

D. at least one mixing blade removably mounted in the mixing vessel and being rotationally driven therein for fully intermixing the components forming the bone cement;

E. movement control means removably mounted in the delivery tube and constructed for receiving the mixed bone cement at the proximal end of the delivery tube and controllably advancing the mixed cement through the delivery tube to the outlet portal; and F. position control means cooperatively associated with the delivery tube and the mixing vessel to enable the delivery tube to be movable from
   a. a first position wherein the interior of the mixing vessel and the interior delivery zone of the delivery tube are sealed from each other, and
   b. a second position wherein the interior of the mixing vessel and the interior zone of the delivery tube are in communication with each other;

whereby the bone cement components are fully intermixed in a separate zone completely sealed from the delivery tube and, once the cement is mixed, the mixing vessel and delivery tube are moved into communication with each other, enabling the mixed cement to be controllably advanced from the mixing vessel to the outlet portal for direct use.

34. The integrated mixing and delivery system defined in claim 33, wherein said position control means are further defined as comprising a pair of radially extending arm members formed on the outer wall of the delivery tube for enabling the controlled movement of the delivery tube between its first and second positions.

* * * * *